United States Patent
Marks et al.

(10) Patent No.: US 9,977,018 B2
(45) Date of Patent: May 22, 2018

(54) ELECTROCHEMICAL LATERAL FLOW BIOASSAY AND BIOSENSOR

(71) Applicants: Nanyang Technological University, Singapore (SG); Ben-Gurion University of the Negev Research and Development Authority, Beer Sheva (IL)

(72) Inventors: Robert S. Marks, Beer Sheva (IL); Polina Brangel, Beer Sheva (IL); Vladislav Papper, Singapore (SG); Evgeni Eltzov, Beer Sheva (IL)

(73) Assignees: NANYANG TECHNOLOGICAL UNIVERSITY, Singapore (SG); BEN-GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 53 days.

(21) Appl. No.: 14/784,859

(22) PCT Filed: Apr. 14, 2014

(86) PCT No.: PCT/SG2014/000163
§ 371 (c)(1),
(2) Date: Oct. 15, 2015

(87) PCT Pub. No.: WO2014/171891
PCT Pub. Date: Oct. 23, 2014

(65) Prior Publication Data
US 2016/0054311 A1    Feb. 25, 2016

Related U.S. Application Data
(60) Provisional application No. 61/811,984, filed on Apr. 15, 2013.

(51) Int. Cl.
*G01F 1/64* (2006.01)
*C12Q 1/00* (2006.01)
(Continued)

(52) U.S. Cl.
CPC ....... *G01N 33/5438* (2013.01); *G01N 33/521* (2013.01)

(58) Field of Classification Search
None
See application file for complete search history.

(56) References Cited

U.S. PATENT DOCUMENTS 6,071,406 A * 6/2000 Tsou ............. B01D 67/0018
                                                           210/500.27
6,478,938 B1   11/2002 Paek et al.
(Continued)

FOREIGN PATENT DOCUMENTS

WO    2013/011323 A2    1/2013

OTHER PUBLICATIONS

Du et al., "Integrated Lateral Flow Test Strip with Electrochemical Sensor for Quantification of Phosphorylated Cholinesterase: Biomarker of Exposure to Organophosphorus Agents," *Analytical Chemistry* 84(3):1380-1385, 2012.
(Continued)

*Primary Examiner* — Eli Mekhlin
(74) *Attorney, Agent, or Firm* — Seed IP Law Group LLP

(57) ABSTRACT

An electrochemical lateral flow biosensor (ELFB) includes an ELFB strip and electronic detector unit coupled to the strip. The strip includes a polymeric hydrophobic membrane, conjugation pad, sampling pad, screen-printed electrode (SPE), and wick pad. The membrane provides a solid support and enables capillary flow along the strip. The conjugation pad is placed on the membrane at one end of the strip and contains adsorbed dehydrated labelled conjugate
(Continued)

particles that are coated with the biorecognition element and coated or filled with the electrochemically active component. The sampling pad is placed on the conjugation pad and provides adsorption of the liquid sample. The SPE is coated with immobilized capture antibodies. The wick pad is placed on the SPE and provides absorption of excess reagents maintaining a lateral flow along the strip. The ELFB can be used for rapid and early detection and quantity analysis of biological liquids and wastewater.

22 Claims, 18 Drawing Sheets

(51) Int. Cl.
  *G01N 17/04* (2006.01)
  *G01N 27/26* (2006.01)
  *G01N 33/50* (2006.01)
  *G01N 33/543* (2006.01)
  *G01N 33/52* (2006.01)

(56) References Cited

U.S. PATENT DOCUMENTS

| | | | |
|---|---|---|---|
| 7,300,802 B2 | 11/2007 | Paek et al. | |
| 7,718,388 B2 | 5/2010 | Baeumner | |
| 2004/0106190 A1 | 6/2004 | Yang et al. | |
| 2009/0081766 A1* | 3/2009 | Fukushima | G01N 33/54353 435/287.1 |
| 2014/0106441 A1* | 4/2014 | Wang | C12Q 1/689 435/287.2 |
| 2014/0113384 A1* | 4/2014 | Kavusi | G01N 33/561 436/501 |
| 2014/0206956 A1* | 7/2014 | Rabinovitz | G01N 33/54386 600/302 |
| 2015/0241379 A1* | 8/2015 | Choudhary | C12Q 1/002 204/403.04 |

OTHER PUBLICATIONS

Ojeda et al., "Electrochemical immunosensor for rapid and sensitive determination of estradiol," *Analytica Chimica Acta* 743:117-124, 2012.

Tudorache et al., "Biosensors based on screen-printing technology, and their applications in environmental and food analysis," *Analytical Bioanalytical Chemistry* 388(3):565-578, 2007.

Wilson, "The use of gold nanoparticles in diagnostics and detection," *Chemical Society Reviews* 37(9):2028-2045, 2008.

Cheng, Y., Master's thesis entitled "Developing Electrochemical Biosensors for Point-of-care Diagnostics of Cardiovascular Biomarkers," Western University, 2013, 118 pgs.

Han, H., Master's thesis entitled "Amplified voltammetric detection of miRNA and the cleavage of peptide by BACEI," Central South University, China, Feb. 15, 2013, 24 pgs, w/ English summary.

Kwon, S. J. et al., "An electrochemical immunosensor using p-aminophenol redox cycling by NADH on a self-assembled monolayer and ferrocene-modified Au electrodes," *Analyst* 133:1599-1604, 2008.

Liu, G. et al., "Disposable Electrochemical Immunosensor Diagnosis Device Based on Nanoparticle Probe and Immunochromatographic Strip," *Anal. Chem.* 79:7644-7653, 2007.

Taleat, Z. et al., "Screen-printed electrodes for biosensing: a review (2008-2013)", *Microchim Acta* 181:865-891, 2014.

* cited by examiner

ELECTROCHEMICAL LATERAL FLOW BIOASSAY AND BIOSENSOR

FIELD OF THE INVENTION

The present invention relates to bioassays and biosensors in general, and to electrochemical lateral flow bioassays and biosensors, in particular.

BACKGROUND OF THE INVENTION

The development of the diagnostic field in the last few decades had a meaningful influence on the improvement occurring in health and medical fields. The progress in diagnostics brought forth a wide variety of efficient and reliable diagnostic tools, which are still considered expensive, complicated to use even for the trained personnel, and available mainly in large medical centres. As such, there is a continuous need worldwide for developing new and improved diagnostic and monitoring tools and techniques, which will at the same time be portable, field operational and provide fast, accurate, direct, quantitative, low cost tests for both viral and bacterial infections, and tumour diagnostics. Over the years the progress in technological devices has led to the development of several prototype biosensors enabling simple, sensitive, specific, and safe detection systems. However, a great potential still lies in the development and improvement of the bioassays and biosensors niche with new and better methods and devices.

Bioassays and biosensors are based on a specific recognition of a particular analyte with any recognition element, such as antibody, antigen, DNA, enzyme, bioreceptor or aptamer, which combines with its specific DNA substrate, antigen or hapten to give an exclusive complex. Antigens are generally high molecular weight proteins, polysaccharides, lipids and polypeptides, which can be detected in different immunoassay configurations. Smaller organic molecules (haptens), such as drugs, simple sugars, amino acids, small peptides, phospholipids, or triglycerides can also be detected, provided that they are chemically coupled to a carrier protein or other synthetic matrices. Thus, just about any analyte can be spotted by the immune system triggering the specific antibody production. Nonetheless, the small molecules (haptens) do not need to be conjugated to a carrier protein or other synthetic matrices, if aptamers are used for detection, instead of antibodies in 'non-sandwich' type assays.

Many types of bioassays have been recently applied to clinical diagnostics, environmental analysis and food safety assessment. Most of them involve synthetic conjugates comprising radioactive, enzymatic, fluorescent, chemiluminescent or visually observable metal sol tags, and specially designed reactor chambers, such as microplates. These assays although being quantitative, such as ELISA, follow long protocols and may takes hours and many reaction steps to complete. They suffer from the relatively high cost and cumbersome procedures, which require expensive instruments and trained personnel.

On the other hand, the lateral flow immunoassay, which is also known as a "strip" test, is an example of a widespread test that is simple to perform by almost anyone and produces results more rapidly than any traditional laboratory-based testing. The coloured lines across the strip can take as little as a few minutes to develop. This area of diagnostics has grown dramatically in recent years, with the most common and well-known of these being the home pregnancy test. Lateral flow immunoassay holds a great diagnostic advantage in the fact that it is cheap, simple for operation, rapid (just a few minutes) and portable. It typically requires little or no sample or reagent preparation. The strips are very stable and robust, have a long shelf life and do not usually require refrigeration. This technique has a wide range of medical diagnostic applications, e.g. ascertain pregnancy, failure of internal organs (e.g. heart attack, renal failure or diabetes), infection or contamination from specific pathogens. In some cases, diseases, such as cancer, can be rapidly detected using the strip test by analysing the blood stream for tumour specific markers, typically, specific antibodies.

The principle of a lateral flow immunoassay relies on the competition for binding sites on a polymer or metal particles. Antibodies that are raised to a specific target are bound to metal nanoparticles or dyed polymer particles. These particles are then applied using an immersion procedure onto a release pad in order to produce a stable particle reservoir for release onto a nitrocellulose-based membrane. Two lines of reagents are immobilised onto the membrane. The target reference or test line comprises a conjugate that can specifically bind the target to be identified and the other, the control, is a line of anti-anti-target antibodies. The release pad and membrane are assembled together with an absorbent pad. The sample is initially added to the adsorbent pad and then the strip is left for a few minutes with the result read directly by eye, looking for the presence of coloured lines. These kits are relatively cheap to make. They also have a long shelf-life and are fully disposable. This technology is, therefore, ideally suited to any rapid diagnostics.

Lateral Flow Immunoassay

R. Wilson (2008) in "*The use of gold nanoparticles in diagnostics and detection*", Chemical Society Reviews 37(9): 2028-2045, reviewed that in their most common form, lateral flow immunoassays consist of porous white membranes striped with a line of antibodies or antigens, and interfaced with antibodies conjugated to labels that can be seen with the naked eye. Reference is initially made to FIG. 1 showing a prior art strip. It should be noted that FIG. 1 relates to prior art knowledge, and as such it merely constitutes a reference for better understanding of the present invention.

Design of the lateral flow device (strip), according to FIG. 1, shows the four major components of the strip (sample pad, conjugate pad, nitrocellulose membrane and wick). TL and CL stand for the test and control lines, respectively. The liquid sample containing the target analyte molecule or entity is applied to the nearest end of the strip, the sample pad or absorbing pad which is located on top of the conjugate pad. The latter contain colorimetric metallic nanoparticles, such as gold nanoparticles (GNPs) or polymeric (e.g., latex) microspheres, coated with the antibodies, which are specific to the target analyte molecules (antigens). The sample migrates through the nitrocellulose membrane by capillary action.

The hydrophobic nitrocellulose membrane serves as a bedding (solid support), onto which anti-target analyte antibodies are immobilised in bands across the membrane in specific areas of the membrane where they capture the analyte and the conjugate as the latter migrate. Essential in the lateral flow immunoassay is the migration of a liquid sample, or its extract containing the analyte of interest, through various zones of the strip where binding molecules have been immobilised that exert more or less specific interactions with the analyte.

As shown in FIG. 1, at least two lines are laid down on the strip: a test line (TL) and a control line (CL), which have both been pre-treated with specific antibodies or antigens, and which is the standard for the commercially available lateral flow strips. The control line may contain either antigens or antibodies that are specific for the conjugate antibodies. Generally, the TL binds the analyte while the CL binds the capture antibody or antigen attached to the red-coloured, coated gold nanoparticles. These lines are usually closer to the wicking pad than to the conjugate pad in order to improve the overall performance of the lateral flow immunoassay. Some lateral flow assays may have more than one test line, but each additional test line greatly increases the complexity of the immunosensor, and thus increases cost.

After absorbing the liquid sample onto the sample pad, the liquid moves into the conjugate pad by capillary action, rehydrates the labelled conjugate particles and allows the mixing of these particles with the absorbed liquid sample. The labelled conjugate interacts with the specific analyte contained in the sample, thereby initiating the intermolecular interactions, which are dependent on the affinity and avidity of the reagents. Then it starts migrating towards the test line capturing and recognising the binding analyte, where it becomes immobilised and produces a distinct signal for example, in the form of a coloured line, indicating the test is positive. Excess reagents move past the capture lines and are entrapped in the wick pad, which is designed to draw the sample across the membrane by capillary action and thereby maintain a lateral flow along the chromatography strip.

Notwithstanding the immediate success of the lateral flow strips, their current applications leave much to be desired. A distinct signal at control line may indicate a proper flow of the body liquid through the strip. Depending upon the analytes present in the sample and on the type of the immunoassay performed, the coloured reagent becomes bound both at the test line and at the control line, or, alternatively, only at the test line. Thus, the results are interpreted on the reaction matrix as the presence or absence of lines of captured conjugate, and are read either by eye or using a reader. These results are unfortunately binary ("yes or no") and do not provide any quantitative measure of the analyte present in the sample. In other words, the major disadvantage of the lateral flow devices is that they are only capable of producing qualitative or semi-quantitative measurements, while a quantitative option can be obtained only using a special and additional instrumentation such as a colorimeter.

In addition, the lateral flow strips suffer from a large number of false positive results. Some lateral flow immunoassays are competitive assays, which differ from the antibody sandwich immunoassays in that the conjugate pad contains antibodies that are already bound to the target analyte. If the target analyte is present in the sample, it will not be able to create the complex with the conjugate and hence, will remain unlabelled. Competitive immunoassays are most suitable for testing small molecules, such as toxins and hormones, and unable to bind to more than one antibody simultaneously. For example, if an excess of the unlabelled analyte is not present, a slightly coloured line may appear in the test line, indicating an inconclusive result.

Failure of the lateral flow immunoassay to provide quantitative results has prompted an urgent need for a new bioassay and biosensor that would allow quantitative measurements within the same simple and miniaturised framework of the current lateral flow strip while maintaining a rapid diagnostics, long shelf life and an easy handling by untrained personnel. With the market value of lateral flow immunoassay kits and devices estimated at approximately 2.1 billion dollars, and with over 200 companies worldwide producing a range of testing formats, many attempts have been made to improve upon these devices. Thus, there is a long-time need for development of a new format for lateral flow assay, which would be quantitative, more sensitive and show no false positive results.

It is therefore an object of the present invention to solve the problems associated with the modern lateral flow assays and biosensors, and to perform the quantitative measurements within the same platform. The present invention solves these problems by successful combination of the lateral flow technology with the electrochemical method in one assay and in a single device. Such integration of the electrochemical method into the lateral flow technology, as described below, produces a quantitative, quick and portable novel platform for a biosensor.

I. Ojeda et al (2012), in "*Electrochemical immunosensor for rapid and sensitive determination of estradiol*", Analytica Chimica Acta 743: 117-124, describes the preparation of an electrochemical immunosensor for estradiol based on the surface modification of a screen printed carbon electrode with grafted p-aminobenzoic acid followed by covalent binding of streptavidin and immobilization of biotinylated anti-estradiol (anti-estradiol-biotin).

U.S. Pat. No. 6,478,938 provides an electrochemical membrane strip biosensor, which combines the immunochromatographic method and electric conductivity detection technology. This biosensor uses gold nanoparticles for the measurement of metal conductivity. The metal colloids generate the quantitative signal in the electrochemical signal generating membrane pad. Thus, the analytical signal of the biosensor is based on metal conductivity of gold nanoparticles.

U.S. Pat. No. 7,300,802 relates to a biosensor comprising a regular membrane strip chromatographic assay system with four membrane pads as described above, and an additional membrane pad for the supply of substrate solution for enzyme. In addition, the strip has a cross-arrangement of two groups of the membrane pads and hence, includes a pad for absorption of vertical flow medium and a pad for absorption of horizontal flow medium. The biosensor shows successive cross-flow procedure for immune reaction and enzymatic reaction, and it uses HRP enzyme to provide the analytical signal. It is a complicated multiple-step test that includes the immunological detection together with the enzymatic reaction, resulting in the electrochemical signal measured with a screen printed electrode.

US 2004/0106190 discloses a flow-through assay device for detecting the presence or quantity of an analyte residing in a test sample. This device contains a fluidic medium, which is in communication with an electrochemical affinity biosensor. The latter utilizes detection and calibration working electrodes that are capable of generating a measurable detection current and communicate with affinity reagents, such as redox mediators and capture ligands. The amount of the analyte within the test sample is determined by calibration of the detection current with the calibration current. This sensor uses a redox enzyme to provide the electrochemical signal.

Dan Du et al (2012), in "*Integrated Lateral Flow Test Strip with Electrochemical Sensor for Quantification of Phosphorylated cholinesterase: Biomarker of Exposure to Organophosphorus Agents*", Analytical Chem. 84: 1380-1385, describes an integrated lateral flow immunoassay strip with an electrochemical sensor device for quantification of exposure to pesticides (organophosphates) and nerve agents. This biosensor is based on the use of antibody to selectively capture the enzyme for enzyme activity assay. The test strip coupled with a portable electrochemical analyser is used for immunoreaction and selective separation of the enzyme from biological samples. The biosensor provides the measurement of the total amount of enzyme (including inhibited and active).

The novel biosensor of the present invention (ELFB—electrochemical lateral flow biosensor) has a totally new design and can easily be applied to various biological systems for the detection of bacterial, parasitic and viral infections, tumours, as well as toxins explosives and other pollutants in wastewater and in biological liquids. All the aforementioned prior art biosensor devices significantly differ from the ELFB in the following:

1. The prior art biosensors do not perform the detection in a single step. The main advantage of the ELFB is the single-step analyte detection, since there is no requirement to chemically treat or label the sample prior to the measurement. On the other hand, the aforementioned assays, which use the redox enzymes, will always require an additional step, in which the substrate will be added.
2. Their electrochemical sensor uses redox enzymes for evaluation of the analyte concentration. The ELFB does not use enzymes. In the ELFB, the amperometric signal is produced by reduction of an electrochemically active component (EAC), the role of which in the electrochemical system is to transfer electrons to the electrode corresponding to its redox potential.
3. The overall design of the prior art biosensors places the detection area in the middle of the nitrocellulose membrane. Because the detection of the analyte is performed during the capillarity flow along the nitrocellulose membrane, the longer the membrane, the better will be the separation and detection, which results in less false positive readings. Hence, the ELFB is designed in a way that it will allow the longest flow time by placing the detection area (modified screen printed electrode) at the end of the strip.
4. The prior art electrochemical biosensors do not use the electroactive beads or Particles. The ELFB novelty is also based on use of the electroactive beads or particles. These beads or particles can be either pre-coated with the electrochemically active component (EAC) or alternatively, can be made electroactive by themselves.

SUMMARY OF THE INVENTION

Various embodiments of the present invention provide devices, systems and methods for bioassay, in general, and for immunoassay, in particular, including the detection of a preselected ligand, antibody or antigen in a liquid sample such as wastewater, body fluid or food sample.

According to one embodiment of the invention, the electrochemical lateral flow biosensor (ELFB) strip comprises:
(a) Polymeric hydrophobic membrane, wherein said membrane provides a solid support and enables the capillary flow along the strip;
(b) Conjugation pad, wherein said pad is placed over and in contact with said membrane at one end of the strip and contains the adsorbed dehydrated labelled conjugate particles,
wherein said conjugate particles are coated with the biorecognition element of the assay and coated or filled with the electrochemically active component (EAC);
(c) Sampling pad, wherein said pad is placed on top of and in contact with said conjugation pad and provides adsorption of the liquid sample;
(d) Screen-printed electrode (SPE), wherein said electrode is coated with the immobilised capture antibodies; and
(e) Wick pad, wherein said pad is placed on top and in contact with said screen-printed electrode (SPE) and provides absorption of excess reagents maintaining a lateral flow along the strip.

According to a specific embodiment, the SPE is either placed over along and in contact with the polymeric strip membrane or screen-printed directly onto said membrane at another end of the strip, opposite to the conjugation pad.

According to another specific embodiment, the SPE comprises one or more working electrodes.

According to another embodiment, the electrochemical lateral flow biosensor (ELFB) device comprises:
(a) The strip according to the embodiments of the present invention placed inside the casing or frame; and
(b) Electronic detector unit, to which said strip is connected using cable or wirelessly.

According to a yet further embodiment, the method for assembling of the ELFB device comprises the following steps:
(a) Preparation of the bioreceptor molecule;
(b) Surface functionalisation of the conjugate particles and immobilisation of said bioreceptor molecule onto the surface;
(c) Preparation of the EAC conjugate particles by either:
  i. Immobilisation of the EAC onto the surface of the conjugate particles (coating) using the known immobilisation techniques; or
  ii. Introduction of the EAC inside the conjugate particles (filling), where said particles being filled are porous polymeric particles capable of releasing said EAC at the electrode through turning the voltage on.
(d) Coating the surface of the conjugate particles with the blocking agent in order to prevent non-specific bindings;
(e) Surface functionalisation of the SPE and immobilisation of the capture antibody onto the surface;
(f) Coating the surface of the SPE with BSA in order to prevent non-specific bindings;
(g) Placing the polymeric strip membrane on the bottom part of the casing or frame;
(h) Dipping the conjugation pad into the liquid mixture of the conjugate particles prepared in steps (a)-(d), drying the conjugation pad and placing it over and in contact with the polymeric strip membrane, at one end of the membrane;
(i) Placing the sampling pad over and in contact with the conjugation pad;
(j) Placing the SPE modified in steps (e)-(f) over and in contact with the polymeric strip membrane, at another end of the membrane, opposite to the conjugation pad;
(k) Placing the wick pad over and in contact with the SPE;
(l) Closing the casing or frame with the upper part (cover) and connecting the electronic detector unit to the SPE.

In another embodiment, the ELFB diagnostic system comprises the ELFB device, an external receiver/recorder able to receive data transmitted by the device, and a computing platform or workstation able to store, process, display, analyse the received data, and transmit the signal and analysed data remotely.

In a specific embodiment, said external receiver/recorder and said computing device can be the same mobile device or cell phone.

According to yet another embodiment, the method for the analysis or diagnostics using the ELFB device comprises the following steps:
(a) Collecting the sample from any tested source, such as wastewater or biological or physiological liquid;
(b) Dropping the sample on the ELFB strip;
(c) Acquiring the amperometric signal with the electronic detector unit; and
(d) Transmitting the acquired amperometric signal or data obtained from the ELFB strip to the external receiver/recorder, and analyzing said signal or data.

Various embodiments of the invention may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The present invention will be understood and appreciated more fully from the following detailed description taken in conjunction with the appended figures. Various exemplary embodiments are well illustrated in the accompanying figures with the intent that these examples not be restrictive. Of the accompanying figures.

Figure 1:
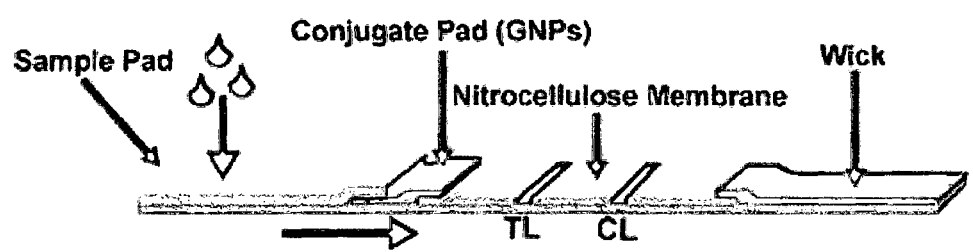
FIG. 1 is a schematic view of a typical prior art chromatography strip used in the lateral flow immunoassay.

It will be appreciated that for simplicity and clarity of the illustration, elements shown in the figures have not necessarily been drawn to scale. For example, the dimensions of some of the elements may be exaggerated relative to other elements for clarity. Furthermore, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

It should be noted that although a portion of the discussion may relate to immunoassay and immunosensor devices, systems, and methods, the present invention is not limited in this regard, and embodiments of the present invention may be used in conjunction with various other sensing, monitoring and analytical devices, systems, and methods. As such, some embodiments of the invention may be used, for example, in conjunction with aptamer technology and aptamer assays, molecular imprints and molecular imprint assays, DNA hybridization, ligand or conjugates, in vitro detection of a substance or a material, detection and quantification of a medical condition or a pathology, acquisition or analysis of data, and/or various other analytical devices and methods. Some embodiments of the invention may be used not necessarily in the context of biosensing.

Figure 2A:
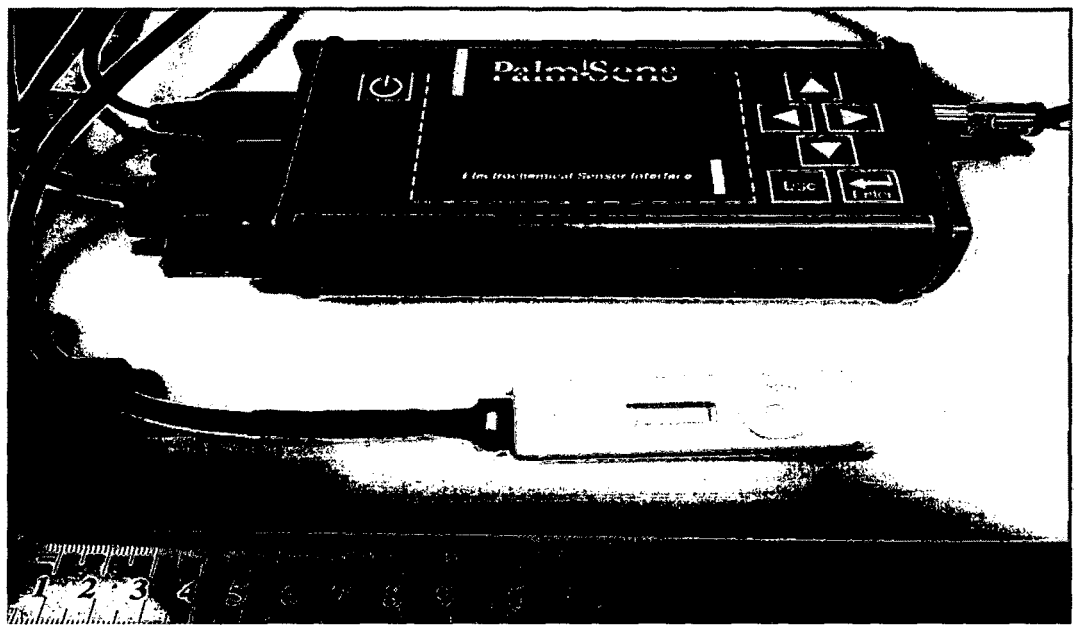
FIG. 2A shows the photo of the ELFB working prototype.
Figure 2B:
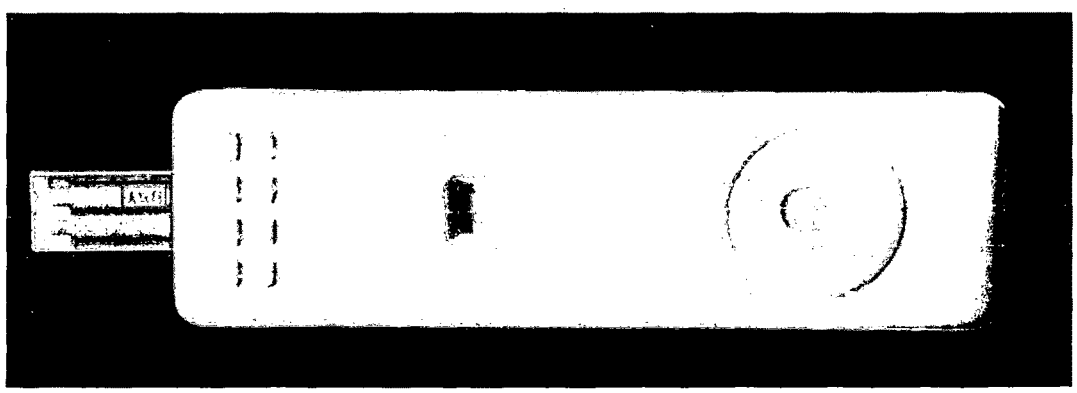
FIG. 2B shows the prototype ELFB strip with the SPE inside the plastic housing.

The electrochemical lateral flow biosensor (ELFB) of an embodiment of the invention comprises the ELFB strip and electronic detector unit. Reference is now made to FIGS. 2A and 2B showing the photo of the ELFB working prototype device and the strip in a plastic housing, respectively. The strip is placed inside the plastic housing and connected to the external electronic detector unit (receiver), which reads the amperometric signal from the ELFB strip. The electronic detector unit can be any commercially available potentiostat or galvanostat with electrochemical sensor interface, such as Ivium PocketStat, DropSense µSTAT 400, Metrohm Autolab PGSTAT204 and 910 PSTAT mini, PalmlSense and EmiStat (by PalmlSense), SP series and SensorStat (by BioLogic), EZStat and PowerStat (by NuVant Systems) and small hand-held PG581 (by Uniscan Instruments) or more appropriately a proprietary device the inventors will build specifically for the present invention including electronic adaptor chip to a cell phone or any other suitable mobile device.

Figure 3:
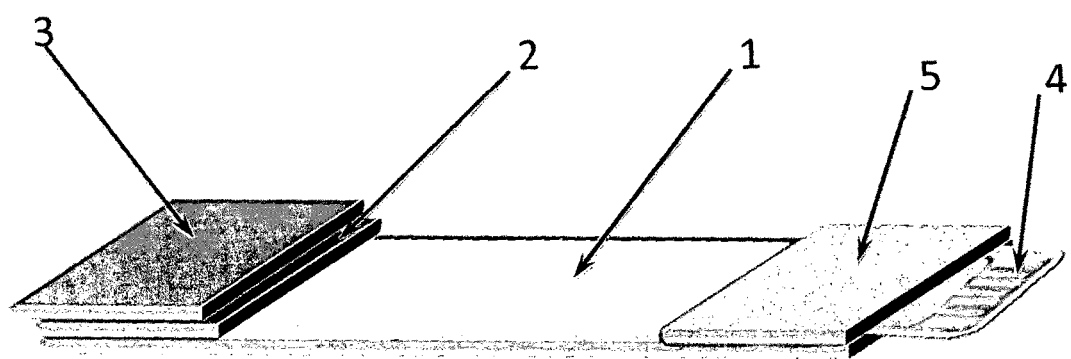
FIG. 3 shows a schematic view of the entire ELFB strip including nitrocellulose membrane, conjugation pad, sampling pad, SPE, and wick pad, constructed and operative in accordance with an embodiment of the present invention.

Reference is now made to FIG. 3 schematically showing the ELFB strip. In one embodiment, the ELFB strip comprises:
 (a) polymeric hydrophobic membrane 1, wherein said membrane provides a solid support and enables the capillary flow along the strip;
 (b) conjugation pad 2, wherein said pad is placed over and in contact with membrane 1 at one end of the strip and contains adsorbed dehydrated labelled conjugate particles,
  wherein said conjugate particles are coated with the biorecognition element of the assay and coated or filled with an electrochemically active component (EAC);
 (c) sampling pad 3, wherein said pad is placed on top of and in contact with conjugation pad 2 and provides absorption of the liquid sample;
 (d) screen-printed electrode (SPE) 4, wherein said electrode is coated with the immobilised capture antibodies; and
 (e) wick pad 5, wherein said pad is placed on top of SPE 4 and in contact with said electrode and provides absorption of excess reagents maintaining a lateral flow along the strip.

Sampling pad 3 is usually made of cellulose, glass fibre, cross-linked silica or other material where the liquid sample is initially added and then subjected to the lateral flow. If necessary, the sampling pad may optionally modify the sample to improve the results of the assay. This might be by modifying pH, filtering out solid components, separating the components of the sample, adsorbing out unwanted particles and compounds or some other test specific variables. For some applications, the sampling pad may be pre-treated by being dipped into a specific buffer containing a mix of a solution comprised of soluble proteins, surfactants, detergents and other polymers. Such buffer allows for a steady lateral flow and prevents nonspecific binding of sample components to the pad.

The screen-printed electrode (SPE) 4 is either placed over along and in contact with the polymeric strip membrane or screen-printed directly onto said membrane at another end of the strip, opposite to the conjugation pad. The example of such silver SPEs printed directly on the nitrocellulose membrane and used in the present ELFB device is shown on FIG. 16.

Figure 4:
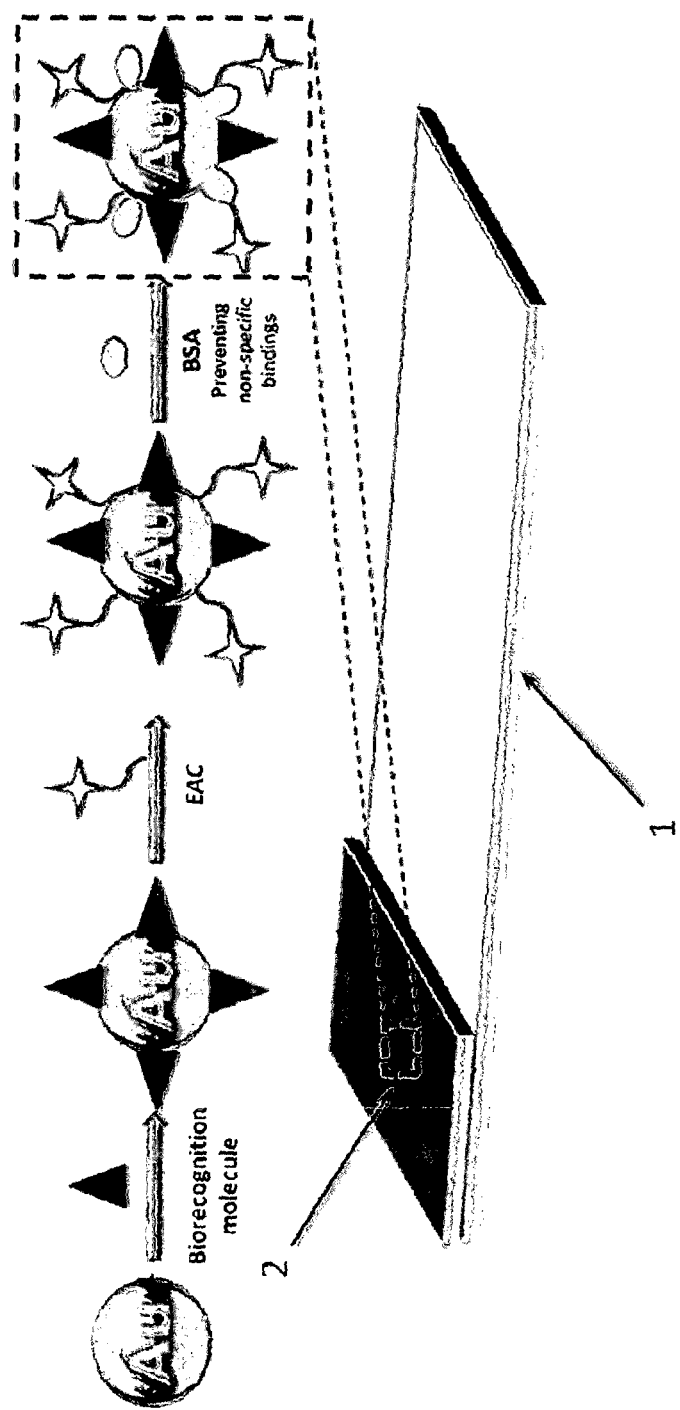
FIG. 4 is a schematic view of two components of the electrochemical lateral flow biosensor (ELFB) strip: nitrocellulose membrane and conjugation pad, the latter is preloaded with the coated particles conjugate, constructed and operative in accordance with an embodiment of the present invention.

Reference is now made to FIG. 4 showing polymeric membrane 1 with conjugation pad 2 over it. The polymeric hydrophobic membrane providing a solid support for the strip is a commercially available porous membrane, which consists of a very thin Mylar sheet coated with a layer of nitrocellulose or cellulose acetate that binds proteins electrostatically through interactions with the nitrate esters and the peptide bonds of the proteins. The benefits of using nitrocellulose or cellulose acetate as a membrane matrix include low cost, good capillary flow, easy handling and cutting, and the ability of manufactures to varying thickness and components of the membrane in order to suit the specific application. For example, 10-20 µm nitrocellulose membrane porous sizes may be chosen in order to suite the size of the particular migrating complex and the time for the formation of the immune detection.

Conjugation pad 2 of the strip is usually made of cross-linked silica, but it may also be made from non-absorbent material such as fibreglass, polyester, rayon or a similar material. The conjugation pad is preferably comprised of a synthetic material (at least when using gold nanoparticles) to ensure the efficient release of its contents. The labelled conjugate particles are typically colloidal gold, or a coloured, fluorescent, or paramagnetic mono dispersed polymeric particles (for example, latex) for visual and optical detection. In principle, any coloured particles can be used. However, commonly either latex (blue colour or colourless) or nanometer sized particles of gold (red colour) are used. The gold particles are red in colour due to localised surface plasmon resonance. Fluorescent or magnetic labelled particles can also be used; however, these require the use of an electronic reader to assess the test result.

The labels are normally of the sizes of 10 nm to 1 mm, allowing an unobstructed flow through the membrane. The labels may be selenium particles, carbon macrocycles or liposomes, besides the aforementioned colloidal gold and coloured latex particles. Brightly coloured, fluorescent or bioluminescent dyes can be incorporated into liposomes, thereby allowing visualization of the response. The newest labels may also include quantum dots or semi-conductor beads.

As shown on FIG. 4, the labelled conjugate particles are initially coated with one of the biorecognition elements of the assay, such as antigen, antibody, bioreceptor, DNA, molecular imprint, ligand, lectin, or aptamer (dependent on the format of the assay). In a particular embodiment, an electrochemically active component (EAC) is then immobilised onto the surface of the labelled conjugate nanoparticles. Finally, the optimal blocking agent (such as bovine serum albumin (BSA), casein or detergents chosen from known commercially available reagents) is adsorbed onto the particles to prevent any additional non-specific bindings during the test, which may produce false positive results. The prepared labelled conjugate particles are added and adsorbed onto the conjugation pad followed by their dehydration.

Pre-treatment of conjugation pad 2 performed in the same way as with sampling pad 3 helps to ensure that the conjugate releases at the proper rate and enhances its stability. The dry conjugate is released from the conjugation pad after its rehydration retaining the stability and detection potential that it had in solution. Sucrose is often used in the drying process as a matrix that assists the dry conjugate to retain these properties, stabilises nanoparticles and facilitates the release of the conjugate from the conjugate pad.

After absorbing the liquid sample onto sampling pad 3, the liquid moves into conjugation pad 2 by capillary action, rehydrates the labelled conjugate particles and allows the mixing of these particles with the absorbed liquid sample. The labelled conjugate interacts with the specific analyte contained in the sample, thereby initiating the intermolecular interactions dependent on the affinity and avidity of the reagents. These interactions will continue during the entire lateral flow process.

Figure 5:
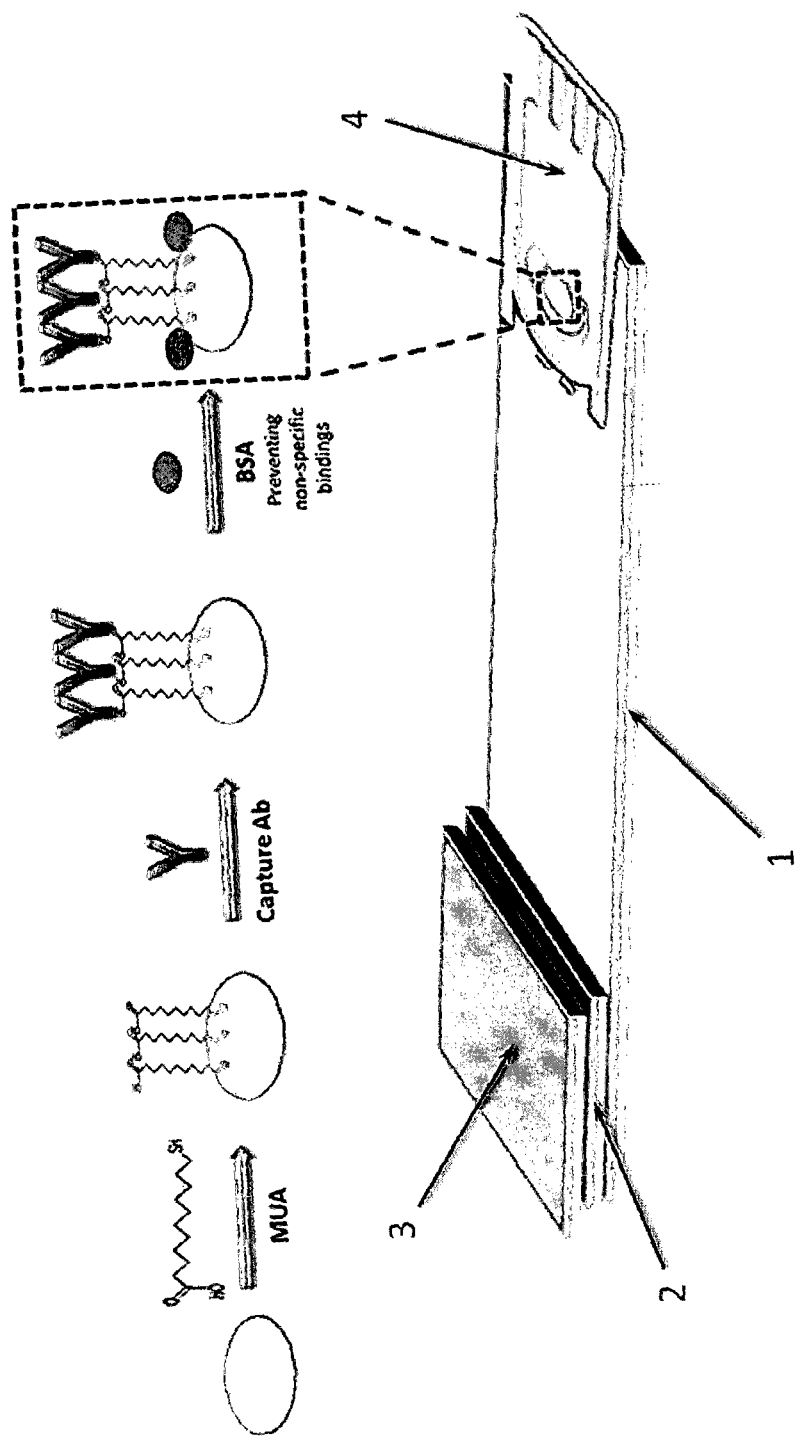
FIG. 5 is a schematic view of four components of the ELFB strip: nitrocellulose membrane, conjugation pad, sampling pad and screen-printed electrode (SPE), the latter is coated with the capture antibody, constructed and operative in accordance with an embodiment of the present invention.
Figure 6A:
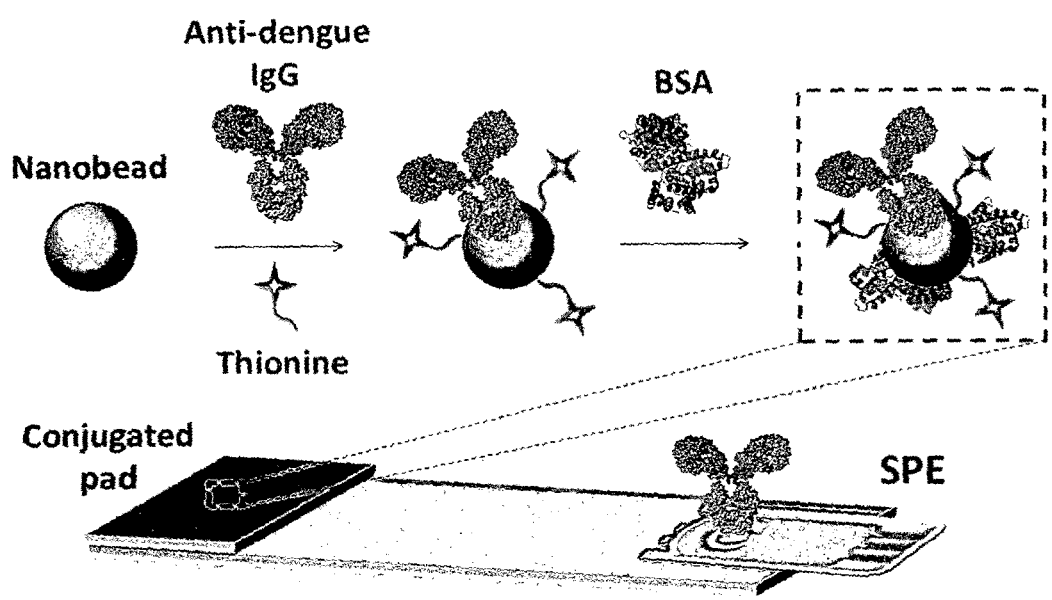
FIG. 6A schematically shows the example of preparation of active polymeric beads or particles coated with the anti-dengue IgG, thionine and bovine serum albumin, and embedded into the conjugated pad. This is the example of an ELFB strip comprising a single working screen-printed electrode (SPE).
Figure 6B:
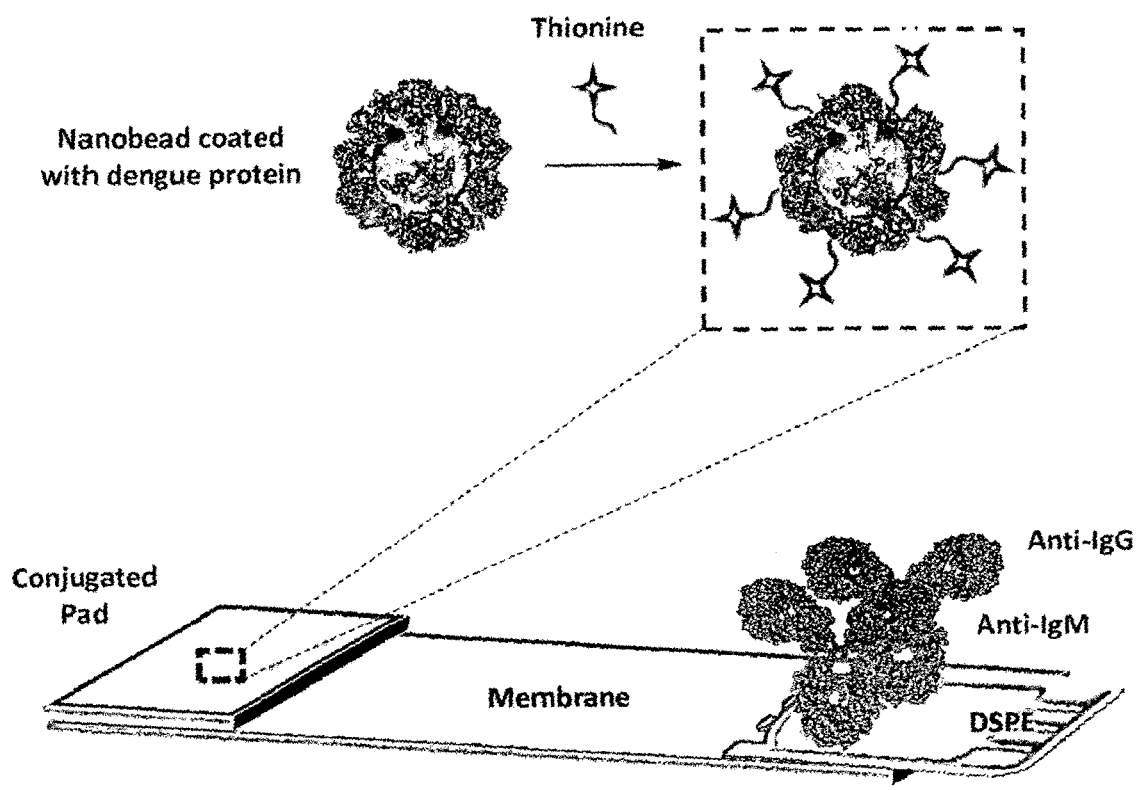
FIG. 6B exemplifies the steps for preparation of active polymeric beads or particles coated with the antigen (for example, dengue protein) and thionine, and embedded into the conjugated pad. This is the example of an ELFB strip comprising a dual working screen-printed electrode (DSPE).

Reference is now made to FIG. 5 showing polymeric membrane 1 with conjugation pad 2, sampling pad 3 and screen-printed electrode (SPE) 4 over it. The electrode is coated with the capture antibody to enable the detection of the analyte in the sample. The example of preparation of active polymeric nanobeads coated with the anti-dengue IgG, thionine and BSA, and embedded into the conjugated pad is shown in FIG. 6A. This is the example of an ELFB strip comprising the single working screen-printed electrode (SPE). FIG. 6B further exemplifies the steps for preparation of active polymeric nanobeads coated with the antigen (dengue protein) and thionine, and embedded into the conjugated pad. This is the example of an ELFB strip comprising the dual working screen-printed electrode (DSPE), as will be detailed below.

Figure 7A:
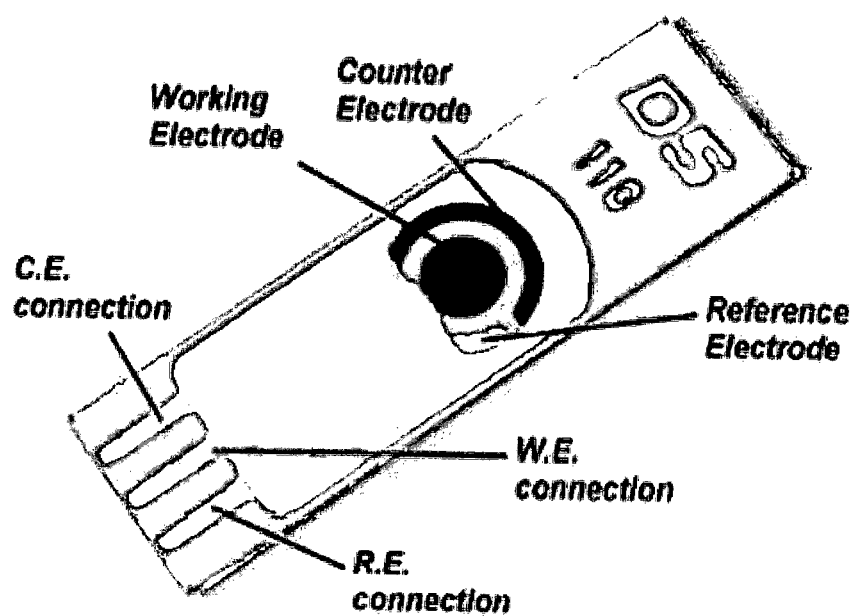
FIG. 7A shows a typical prior art three-electrode system screen-printed electrode by DropSense, described in M. Tudorache and C. Bala (2007), *"Biosensors based on screen-printing technology, and their applications in environmental and food analysis"*, Analytical Bioanalytical Chemistry 388(3): 565-578.

Reference is now made to FIG. 7A, which shows the new generation of a prior art SPE by DropSense designed with three electrodes. It should be noted that FIGS. 7A and 7B relate to prior art knowledge, and as such they merely constitute a reference for better understanding of the present invention.

As shown on FIG. 7A, the first of the three electrodes is the indicating electrode also known as the test or working electrode (WE). This is the electrode at which the electrochemical phenomena (reduction or oxidation) being investigated are taking place. The second functional electrode is the reference electrode (RE). This is the electrode whose potential is constant enough that it can be taken as the reference standard against which the potentials of the other electrodes present in the cell can be measured. The final functional electrode is the counter or auxiliary electrode (CE), which serves as a source or a sink for electrons so that current can be passed from the external circuit through the cell. In general, neither its true potential nor current is ever measured or known.

The thick-film screen-printing technique is widely used for commercial large-scale fabrication of disposable biosensors with several advantages including low cost, versatility, and miniaturization. The biosensors, which are based on the screen printed electrodes, present miniature systems enabling in-vivo and in-vitro analyses of real samples by use of electrochemical devices.

Figure 7B:
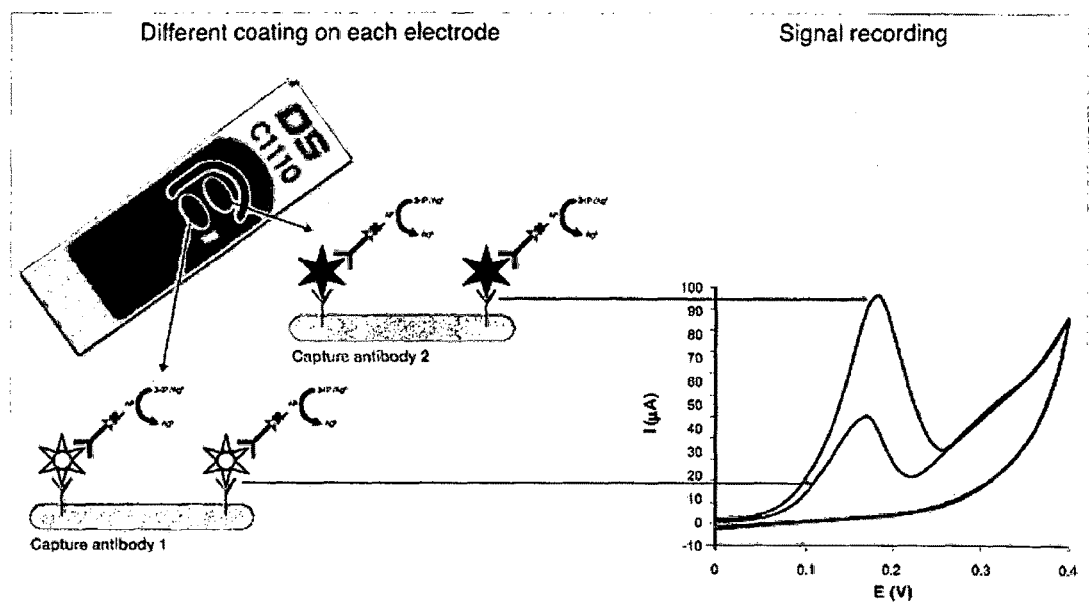
FIG. 7B schematically shows simultaneous detection of two different types of antigens using two pairs of capture antibodies against them. New dual screen-printed electrodes (DSPE) with two elliptic working electrodes, a counter electrode and a reference electrode, developed by DropSense, allow simultaneous detection of two types of species and quantification of their ratio. Alternatively, one of the working electrodes can be used as a control and another one as a testing electrode (Courtesy of DropSense).

The SPE may comprise more than one working electrode. Reference is now made to FIG. 7B, which schematically shows simultaneous detection of two different types of antigens using two capture anti-antibodies against them. The new dual screen-printed electrode (DSPE) with two elliptic working electrodes, a counter electrode and a reference electrode, developed by DropSense, allow simultaneous detection of two different types of antibodies and quantification of their ratio. Alternatively, one of the working electrodes can be used as a control and another one—as a testing electrode.

In order to obtain an amperometric signal, the ELFB device comprises an electrochemically active component (EAC). The role of the EAC in electrochemical system is to transfer electrons to the electrode corresponding to its redox potential.

A large variety of EACs is now available commercially. In order to choose the proper EAC compound for the biosensor applications, one should take into account the following considerations. Firstly, the working electrode potential is relatively low in most of the biological systems. Secondly, the measurements are performed with small volume samples (that means the EAC must be reactive in low amounts). Thirdly, the EAC must be able to bind to the conjugate particles, such as gold nanoparticles or polymeric particles. The examples of EAC, which are commonly used as electrochemical mediators, are Ferrocene, Thionine and Methylene Blue.

As the EAC transfers electrons to the SPE under its reduction potential, the detection efficiency of the SPE depends on the distance between the EAC and the working electrode. Hence, the measurement of the EAC reduction reaction potential enables the detection and quantification of the analyte complex through the immobilized capture antibody. As such, compared to the redox enzyme based assays, in which the analyte detection is based on the produced amperometric signal by a linked redox enzyme, the present invention is based on measurements of the amperometric signal as a result of bringing the EAC close enough to the working electrode to measure the generated current. The latter is proportional to the amount of the analyte in the sample.

Excess reagents are entrapped in the wick pad, which maintains a lateral flow along the strip. The wick pad may be made from non-woven, cellulose fibre sheets. These pads can be manufactured in a variety of thicknesses and densities to suit the needs of the bioassay.

The whole chromatography strip may be made of, for example, a pad or other support structure, such as a flat piece or a unit of another shape, coated with or impregnated or otherwise including nitrocellulose or any other polymer suitable for a chromatographic process. The strip may be in a form of a plain narrow piece (i.e. "strip-shaped"), or may not necessarily be strip-shaped (e.g., if the flow is capillary creeping flow). It may, for example, be coil-shaped in order to increase its length in the same volume, and hence, improve separation of the components of the liquid sample.

Figure 8:
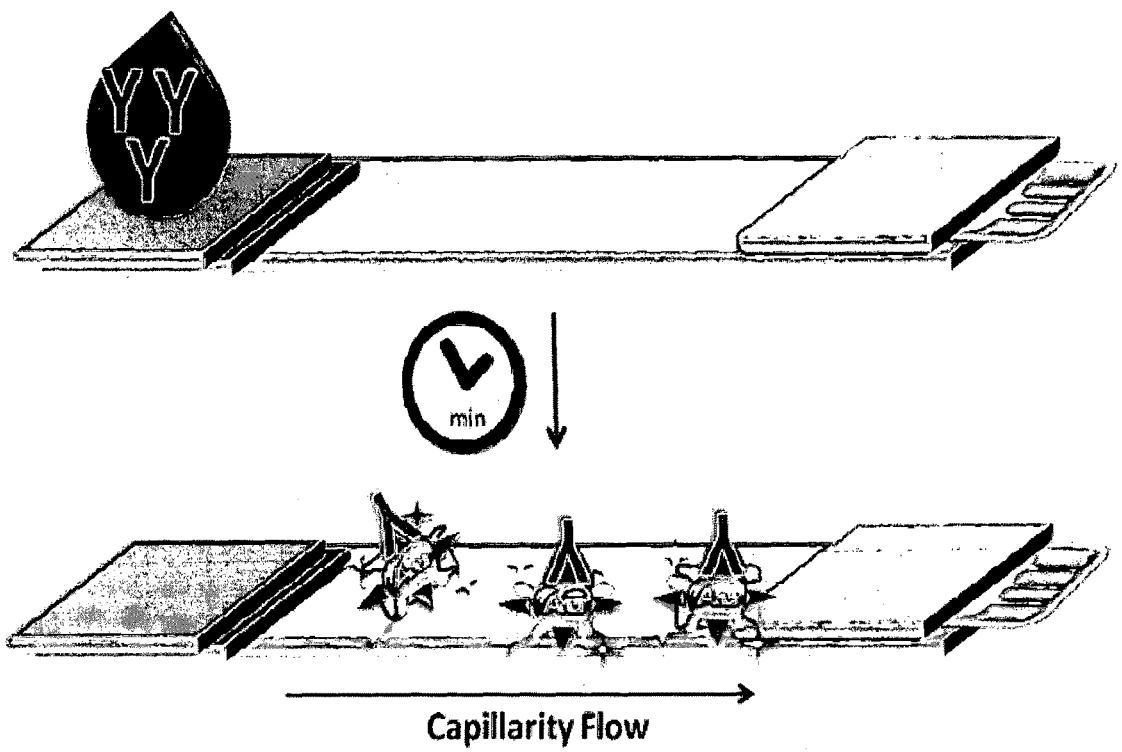
FIG. 8 shows a lateral flow along the ELFB strip, constructed and operative in accordance with an embodiment of the present invention.

Reference is now made to FIG. 8 schematically showing an operational principle of the ELFB strip. The liquid sample containing a tested analyte, such as antigen or antibody is added onto the sampling pad, passes to the conjugate pad, and initially reacts with a biorecognition element, such as antigen, antibody, aptamer or DNA (dependent on the format of the assay), which is immobilised on the surface of the conjugate particles. The resultant complex conjugate particles continue to progress along the strip until they reach the SPE, which is connected to an external electronic detector unit, as shown on FIG. 2A.

Figure 9:
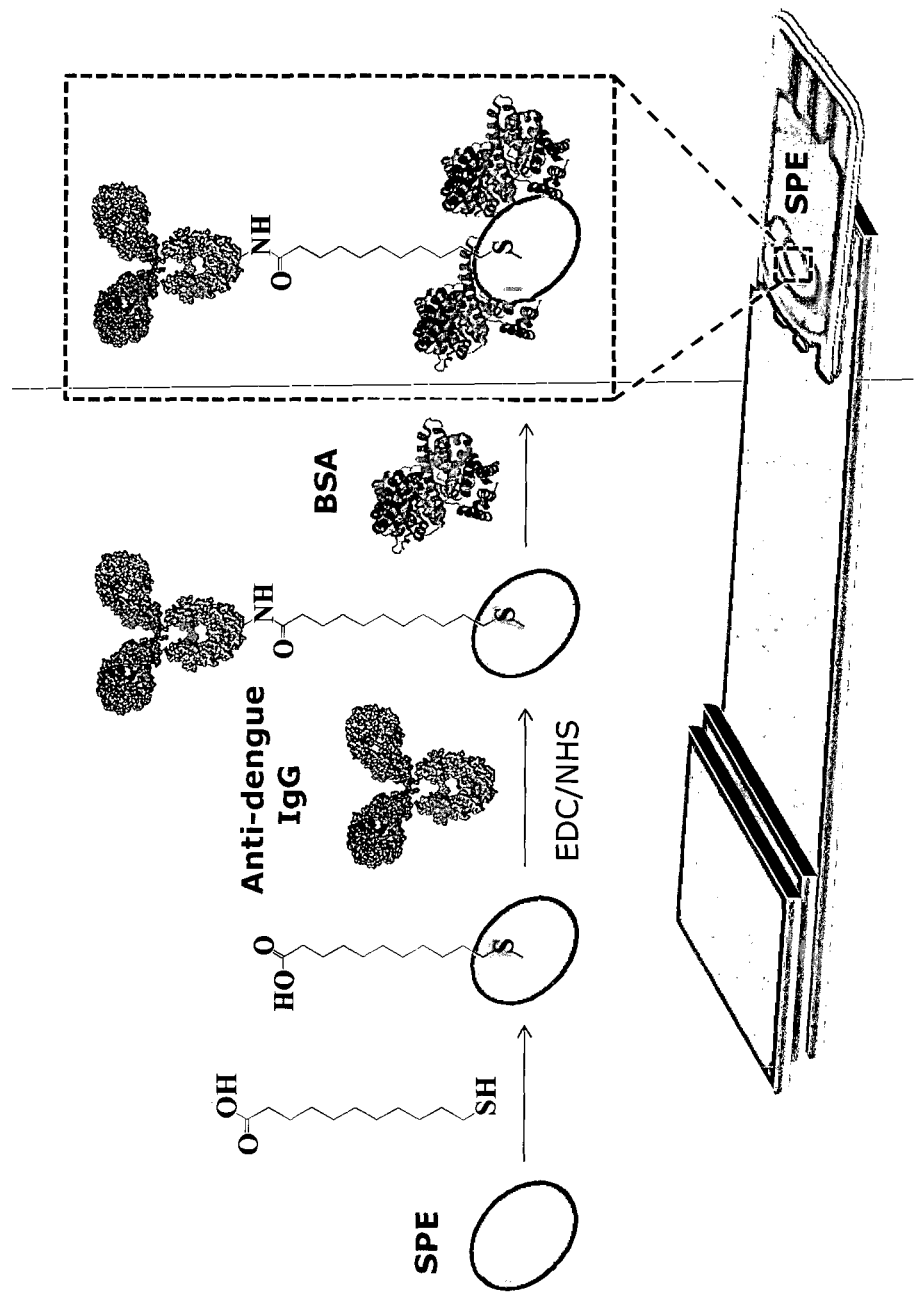
FIG. 9 schematically shows general steps for coating the SPE with the secondary (capture) antibodies.

Reference is now made to FIG. 9 schematically showing the general steps for coating the SPE with the secondary (capture) antibodies. This procedure is exemplified in the experimental section "Immobilization of the capture antibody on the SPE gold surface". Different techniques can be used to immobilize the antibodies on the electrode surface, as well as different crosslinkers, including but not limited to thiols, which have a strong tendency to be chemisorbed onto metallic surfaces, such as when they are used to form the self-assembled monolayers (SAMs).

Immobilization to the metallic surface through thiol derivatives is the most popular way of bioconjugation and is well described in the literature. The simple protocol for manufacturing, dense and oriented layer formation, and relative ease of biomolecules attachment make thiols, undoubtedly, leading molecules in the biosensor field. Thiols are among the most successfully employed chemicals for modification of metal surfaces because of their strong affinity to different metallic surfaces. Thiols react chemically with gold, silver, and copper, forming very stable metal-sulphur bonds.

In addition, functional groups attached to the end opposite to the thiol group control the surface properties of the formed monolayers. The flexibility to design different head groups of monolayers using a large number of functional groups makes this functionalization strategy especially useful for the controlled fabrication of structurally ordered assemblies of proteins on electrode surfaces. Therefore, one of the most important applications of monolayers of functionalized alkanethiols is the binding of many different molecules, which cannot be directly attached to an unmodified metallic surface.

The strong thiol-metal bond formation has been exploited in numerous applications, including the immobilization of DNA on metal surfaces for the generation of DNA microarrays, preparation of the metal electrodes for measuring charge migration mediated by double stranded DNA, and immobilization of antibodies or antigens. Understanding the benefits and disadvantages of using various types of thiols, such as mono-, di-, triple, or mixed thiol molecules, can help choose the right molecule for the specific purpose of immobilization.

Other methods, such as chemisorption, which do not include the modification of metal electrode through thiol groups, can also be used in the present invention. Nevertheless, self-assembly of alkyl thiol monolayer on gold is one of the most promising techniques, which helps to understand interactions of proteins and other biomolecules with artificial substrates. The ease, with which a conjugation complex can be presented in a controlled environment, combined with simple methods that can pattern the formation of SAMs in the plane of the formed monolayer, make these surfaces well suited for studies of fundamental aspects of biointerfacial science, and they are well described in the literature.

Figure 10:
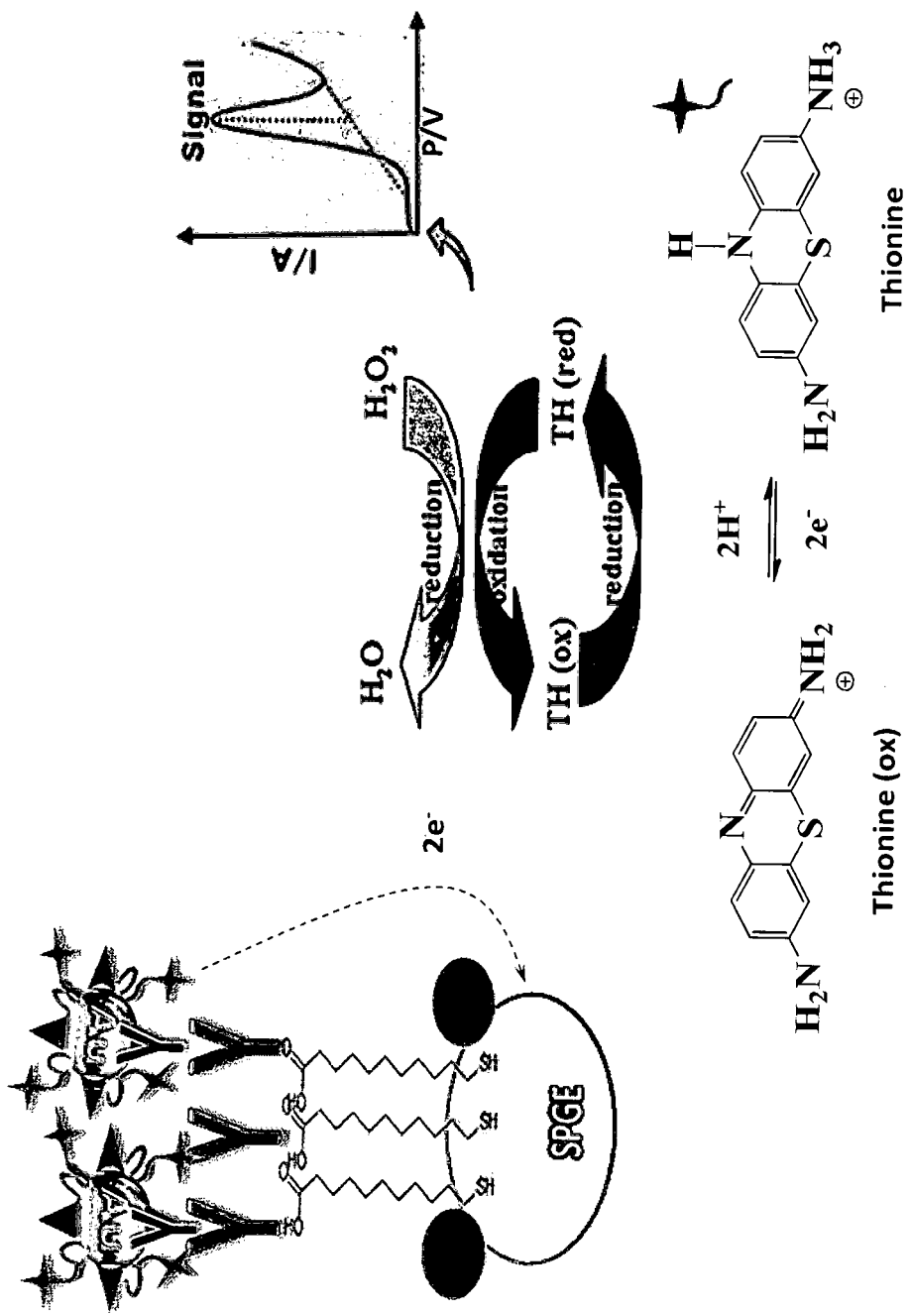
FIG. 10 shows an electrochemical detection principle of the ELFB, exemplified as an oxidation-reduction reaction of thionine at the SPE, generating the electrical current.

FIG. 10 shows an electrochemical detection principle of the ELFB, exemplified as an oxidation-reduction reaction of thionine at the SPE, generating the electrical current. When the conjugate particles containing the EAC and the complex of the biorecognition element with the target analyte reach the SPE, the target analyte element reacts with the specific capture antibodies immobilised on the electrode, and binds the particle to the SPE. The EAC, or specifically thionine, as an example, then transfers the electrons to the electrode under its reduction potential, and the galvanometric signal is transmitted to the detector unit. The received amperometric signal is essentially proportional to the analyte concentration.

In a further embodiment, method for assembling of the ELFB device comprises the following steps:
(a) Preparation of the bioreceptor molecule using the known biochemical techniques;
(b) Chemical modification/surface functionalisation of the chosen conjugate particles and immobilisation of said bioreceptor molecule onto the surface using the known immobilisation techniques;
(c) Preparation of the EAC conjugate particles by either:
  iii. Immobilisation of the EAC onto the surface of the conjugate particles (coating) using the known immobilisation techniques; or
  iv. Introduction of the EAC inside the conjugate particles (filling), where said particles being filled are porous polymeric particles capable of releasing said EAC at the electrode through turning the voltage on.
(d) Coating the surface of the conjugate particles with the blocking agent in order to prevent non-specific bindings;
(e) Chemical modification/functionalisation of the SPE surface, followed by immobilisation of the capture antibody onto the surface using the known immobilisation techniques;
(f) Coating the surface of the SPE with the blocking agent in order to prevent non-specific bindings;
(g) Placing the polymeric strip membrane on the bottom part of the frame, as shown on FIG. 11;
(h) Dipping the conjugation pad into the liquid mixture of the conjugate particles prepared in steps (a)-(d), drying the conjugation pad and placing it over and in contact with the polymeric strip membrane, at one end of the membrane;
(i) Placing the sampling pad over and in contact with the conjugation pad;
(j) Placing the wick pad over and in contact with the SPE;
(k) Closing the frame with the upper part (cover) and connecting the electronic detector unit to the SPE.

The EAC immobilised onto the surface of the conjugate particles can be optionally in a conductive polymeric form. The SPE is either placed over along and in contact with the polymeric strip membrane or screen-printed directly onto said membrane at another end of the strip, opposite to the conjugation pad. The SPE may comprise one or more working electrodes, dependent on the particular application.

The overall amperometric signal obtained from chemical reduction of the EAC modified particles at the SPE can be significantly amplified by using ferrocene as an electrochemically active compound instead of thionine. For the ferrocene-modified nanoparticles, the interfacial potential is determined by the redox state of ferrocene in the presence of hexacyanoferrate ions, which are widely used as the redox enhancers due to their high reactivity with ferrocene compounds on the metallic electrodes.

Thus, the ELFB is based on the detection of the labelled conjugate with an electrochemically active component that produces an amperometric signal. A screen-printed electrode technology is chosen in order to minimize and simplify the use of the device of the present invention. The screen-printed electrode is placed at the end of the strip membrane in order to maximise the reaction time between the biorecognition element and analyte. The novel design of the lateral flow strip provides high integration with the commercially available SPE. The control line of the regular lateral flow strip can be entirely omitted, while the test line corresponds to the surface of the SPE working electrode coated with the antibody that is able to capture the analyte. Alternatively, the control area can be created on the membrane behind the working electrode or on the second working electrode, if DSPE (shown on FIG. 7B) is used. In addition, the overlapping section between the sampling pad and the polymeric membrane is enlarged in order to increase the efficiency of the biorecognition element-analyte complex formation.

In a further embodiment, the ELFB can be used for detection of various proteins, toxins, hormones, explosives, pollutants and other biologically and ecologically important analytes in wastewater and in biological liquids.

There are different types of the bioassay, such as "double antibody sandwich" and "competitive assay", available in diagnostics. The most common assay which can be applied in the ELFB device is a direct assay performed with two antibodies, wherein the first antibody is actually an analyte in the sample to be tested, and it binds to the antigen immobilised on the surface of the conjugate nanoparticles. In this case the second capture antibody immobilised on the electrode surface, is specific for the analyte antibody moving with the conjugate complex along the strip. This method works well for the proteins and big molecules, as will be shown in examples.

Competitive assays are primarily used for testing small molecules, such as toxins and hormones, and are generally unable to bind to more than one antibody simultaneously due to the fact that there may only be one epitope available. The competitive assays differ from the double antibody sandwich immunoassay in that the conjugation pad contains particles with the immobilised antibodies that are already bound to the target analyte. If the target analyte is present in the sample, it will not be able to create the complex with the conjugate and hence, will remain unlabelled. As the sample migrates along the strip and reaches the SPE, an excess of the unlabelled analyte will bind to the immobilised antibody and block the capture of the conjugate particles, so that no amperometric signal is produced. Thus, the competitive format is mainly suitable for testing the calibrated ELFB when the concentration of the analyte in the sample is already known. This format requires a parallel control and its disadvantage is that a positive answer would provide a negative signal.

The sandwich assay application for the ELFB can utilise aptamers, molecular imprints, ligands, lectins, DNA, immunoreagents or bioreceptors. In this case, the biorecognition element is an aptamer that is immobilised on the surface of the conjugate particles and binds the analyte molecules from the sample. The double sandwich assay with two antibodies is another format, which can be used with the ELFB device for the detection of a particular analyte in the sample.

In a specific embodiment, the ELFB can be used for detection of bacterial, viral infections, tumours, as well as toxins, explosives and other pollutants in wastewater and in biological liquids.

Experimental Examples

Preparation of Colloidal Gold Labelled with GIPC1 Protein and Thionine 40 nm colloidal gold solution was adjusted to pH 7.0 with 0.2 M sodium carbonate/0.1 M HCl. 5 ml of GIPC1 solution at the optimum concentration of 40 µg/ml was incubated with 50 ml of colloidal gold solution (pH 7.0) for 2 hours at RT. 5 ml of Thionine at the optimum concentration of 10 µM was incubated with the GNPs (gold nanoparticles)-GIPC1 solution. Blocking of the GNPs was performed by addition of 2 ml of 1% (w/v) BSA in DDW in two steps. After each step, the mixture was incubated at room temperature for another 60 minutes. Finally, to cushion, the labelled particles 0.5% PEG was added to the conjugate. In order to remove the non-conjugated components, the solution was centrifuged (25000×g) at 10° C. for 45 minutes. The pellet was then re-suspended with 50 mM sodium borate (pH 7.0) and stored at 4° C. for use.

Preparation of the Membrane and Conjugation Pad

A 10 µm nitrocellulose hydrophobic membrane (Millipore) was used and cut into 5 mm sections with a CM4000 Guillotine Cutting. The deposition of the test and control lines was done with a computerized manipulator device (MP-285 Micromanipulator System) in order to achieve high accuracy. The conjugate solution containing the colloidal gold labelled with GIPC1 and Thionine was diluted with re-suspension buffer that contained 50 mM sodium borate, 1% (w/v) BSA and 9% (w/v) sucrose (Sigma), pH 7.0 to $OD_{530}$=3. A conjugation pad (Millipore) was made by dipping 5×4 mm glass fibre in the conjugate solution, and then dried for 1 hour at 370° C. The obtained conjugation pad was stored in the presence of desiccant gel at room temperature.

Immobilization of the Capture Antibody on the SPE Gold Surface

The SPE gold working electrode (BioAnalytics) was modified with the immobilization of the HRP conjugated donkey anti-goat (Santa Cruz Antibodies) including the following steps. Initially, the electrodes were pre-treated with a 50 µL of 0.1 M $H_2SO_4$ placed on the SPGE, and cyclic voltammograms from 0 to +1.25V were recorded, using a scan rate of 100 mV/s. After that, the electrodes were washed using DDW and dried. A standard optimal immobilization process was performed. In the first step of the immobilization process, the electrodes were placed in 10 µM 11-mercaptoundecanoic acid (Sigma 450561) (MUA) dissolved in 99% ethanol, and then incubated for 24 hours at RT with 200 RPM. Afterwards, the electrodes were rinsed several times with ethanol and dried. The terminal carboxylate group of MUA was activated with 30 minutes of incubation in a 1:1 mixture of 50 mM N-hydroxysuccinimide (NHS), and 50 mM N-ethyl-N-(3-diethylaminopropyl) carbodiimide (EDC) (Biacore AB Uppsala, Sweden). The electrodes were placed in 1 ml of horseradish peroxidase (HRP) conjugated donkey anti-goat (Santa Cruz Antibodies) diluted to 1:4000 in PBS, and incubated for overnight at 40° C. with 200 RPM. Following, the electrodes were rinsed in PBS several times. Finally, the electrodes were placed in 1 ml of 5% BSA (w/v) for 1 hour at 40° C.

Capture Antibody Immobilization Validation

The SPE electrode was placed in 48 micro wells plate. Then, 90 µL of 3,3',5,5'-tetramethylbenzidine (TMB) liquid substrate system for ELISA (sigma T0440) was added on top of each SPE and the plate was incubated for 30 minutes at 37° C. After that, 90 µL of stop reagent for TMB substrate (Sigma S5814) was added on top of the electrodes, the electrodes were taken out of each well and the absorbance of product solution was determined using 630 nm wavelength at the plate reader.

Integration Assembly of the ELFB Strip and Amperometric Signal Test

Figure 11:
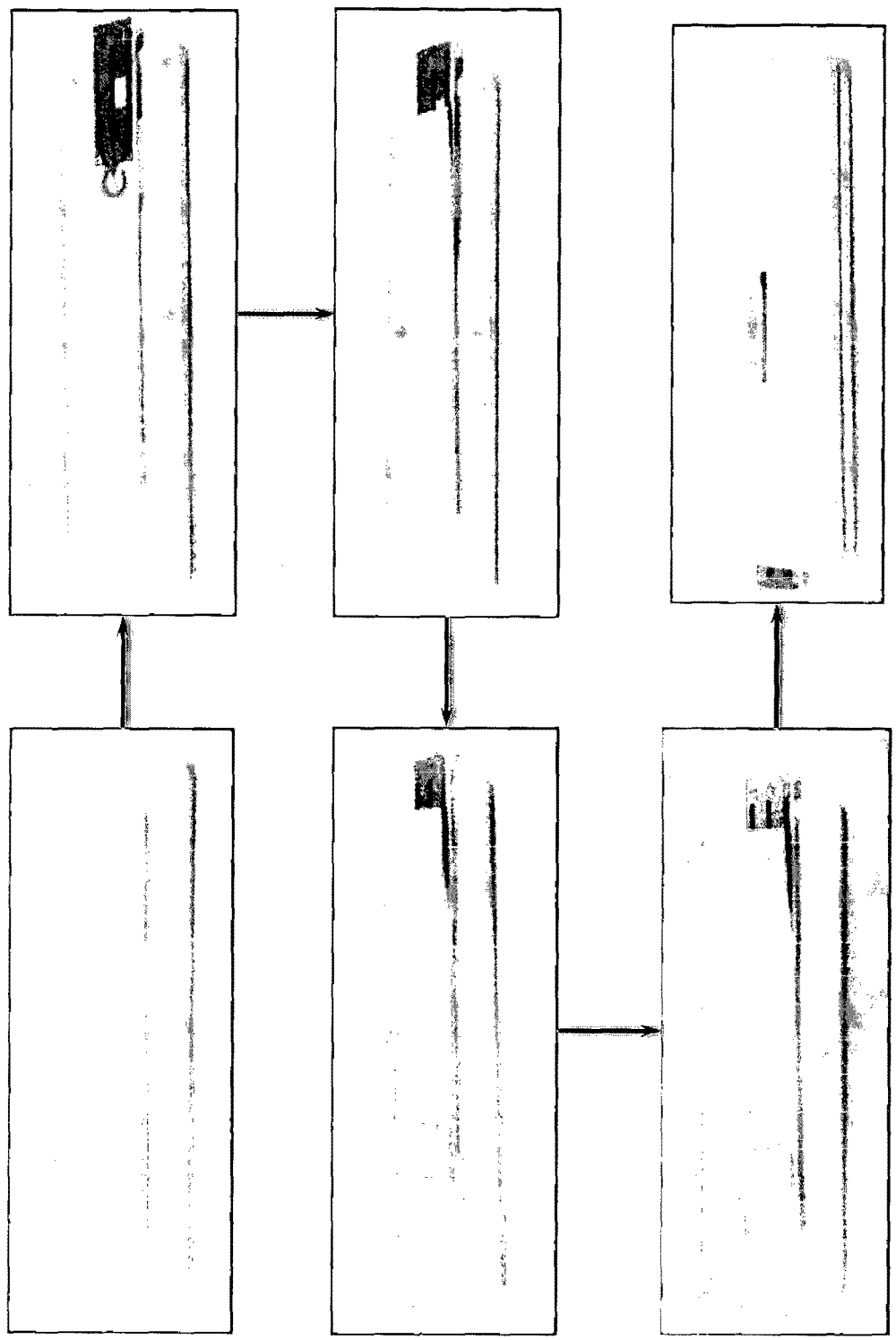
FIG. 11 shows the photos of a general assembling method for the ELFB strip inside the frame.

The lateral flow card was assembled on a frame (plastic backing plate), as shown in FIG. 11. The 10 µL polyester-backed nitrocellulose membrane (Millipore), conjugation pad (Millipore) and sampling pad (Millipore) were pasted accordingly with 1 mm of overlap between the parts. On another side of the membrane, the modified SPE (with immobilized HRP conjugated donkey anti-goat diluted 1:4000) was taped in line with the flow direction. The SPE was covered with the wick pad. 3 mm from the end of the wick pad, 1 µL of epoxy glue was spread in order to prevent penetration of the liquids in the potentiostat connector cable. The obtained strips were stored in the presence of desiccant gel at room temperature. The assembly of the ELFB device is presented in FIG. 2.

The Electrochemical Measurement

100 µL of goat anti-GIPC1 sample was added on the sampling pad of the assembled ELFB device. Equilibrium time of the Palm|Sense software was set to 2.5 min. CV was recorded for each setup using 100 mV/sec scanning rate and scanning from −0.4V to 0.4V. Then, the amperometric signal was evaluated from the pick area of the Thionine reduction potential (approximately −0.24V) by using the three points method of the PSTrace software for Palm|Sense. Mean values and standard deviation were calculated for each record of the amperometric signal.

Figure 12A:
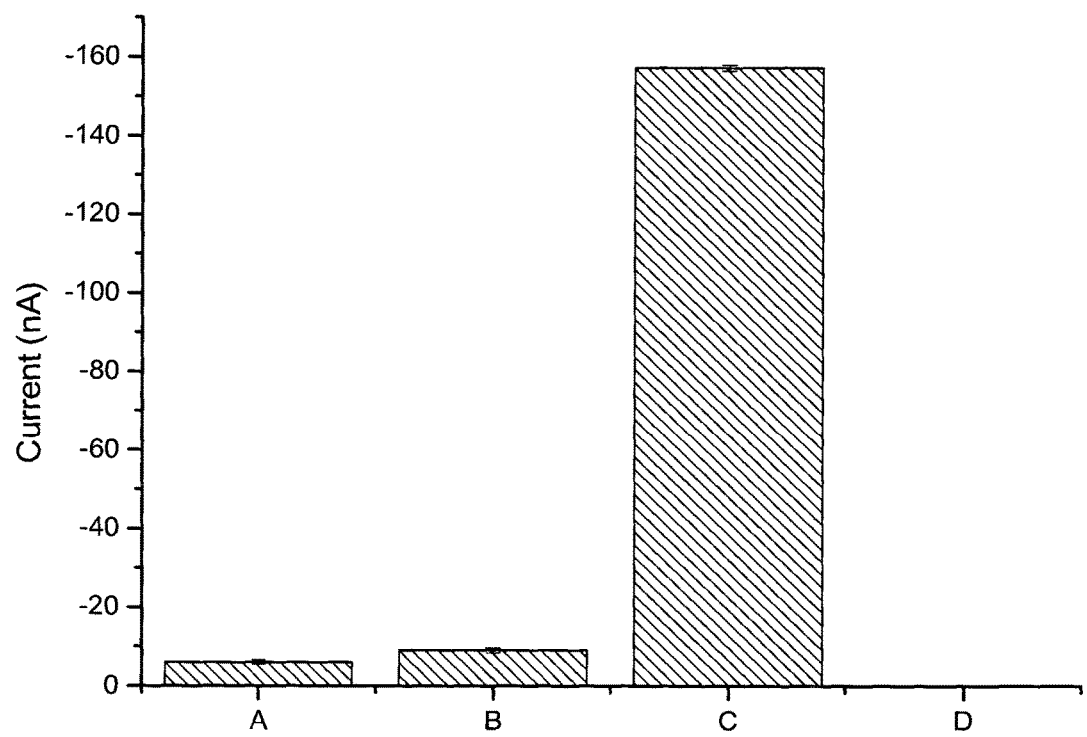
FIG. 12A shows the experimental effect of the SPE modification on the obtained amperometric signal: (A) Bare gold SPE; (B) Gold SPE modified with an immobilized MUA cross-linker; (C) Gold SPE modified with an immobilized capture antibody; and (D) Gold SPE modified with physically adsorbed capture antibody. The amperometric current was obtained from the reduction potential of thionine (approximately 0.24V) at scanning rate of 100 mV/sec. The amperometric signal obtained from (C) is significally higher compare to (A) and (B). T-test was on the mean obtained with a P-Value <0.05. Bars indicate means±standard deviations (n=4).

Reference is made to FIG. 12A, which shows that the amperometric signal by ELFB was produced due to the attachment of the conjugate complex to the SPE through the immobilized capture antibody. The anti-GIPC1 was diluted to 1:500 and added to each one of the ELFB setup. As shown in FIG. 12A, the ELFB setup with the SPE, which physically adsorbed the capture antibody (D), produced no amperometric signal. The absence of the amperometric signal in this setup might indicate the difficulty of the electrons to reach the electrode as a result of the chaotic adsorption of the antibodies, which are buried on the gold surface. For comparison, the ELFB with the immobilized antibodies (via MUA crosslinker) produced 10 times higher amperometric signal compared to the signal of a bare or the MUA modified SPE. The amperometric signal obtained from (C) ELFB setup is significally higher compare to (A) and (B). T-test was on the mean obtained with a P-Value <0.05. Bars indicate means±standard deviations (n=4).

Scanning Electron Microscope

Figure 12B:
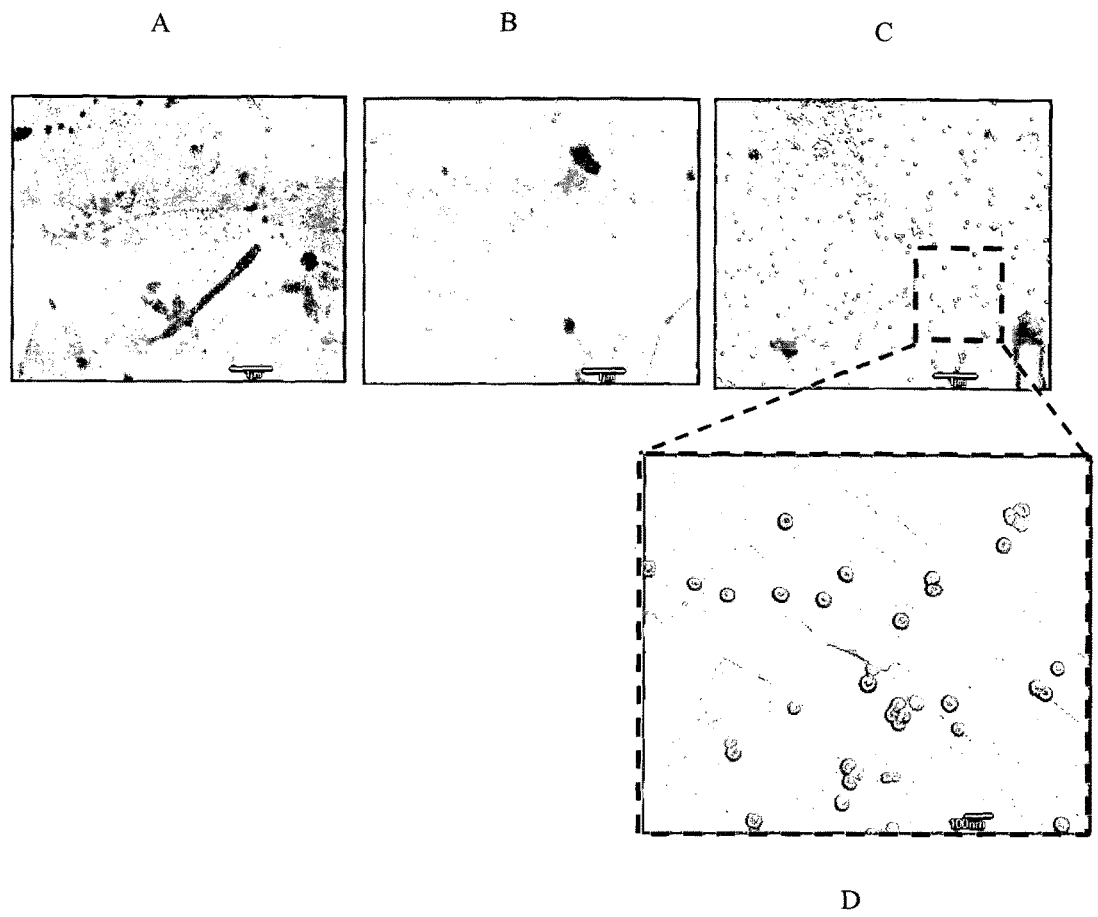
FIG. 12B shows the SEM images of: (A) Bare gold SPE; (B) Gold SPE modified with an immobilized MUA cross-linker; (C) Gold SPE modified with an immobilized capture antibody; and (D) enlarged (C). Accelerating Voltage is 1.5 kV.

FIG. 12B shows the SEM of the modified SPE according to embodiments of the invention. The SEM imaging was done by using a Scanning Electron Microscope JSM-7400F under the company protocol. The modified electrode containing the conjugate complex was rinsed with PBS and dried. The, the electrodes were visualized by using accelerating voltage of 1.5 kV parameter. The light round shaped particles in (D) were visualized on the gold working electrode with the immobilized capture antibody and indicated the attached GNPs. The electrodes with no capture antibody show no presence of the GNPs.

Examination of the Specificity of the Amperometric Signal

In order to ensure that the amperometric signal of the ELFB was specific to the reduction of Thionine and that no other component of the system could contribute to the generated signal, two ELFB setups were established. The only difference between the setups was the labelling of the GNPs. In the first setup, the GNPs were labelled with 40 µg/ml GIPC1 and 10 µM Thionine, while in the second setup, the GNPs were labelled with only 40 µg/ml GIPC1 (can be referred as the background noise). 100 µL of anti-GIPC1 was diluted to 1:3000 and added to each ELFB setup.

Figure 13:
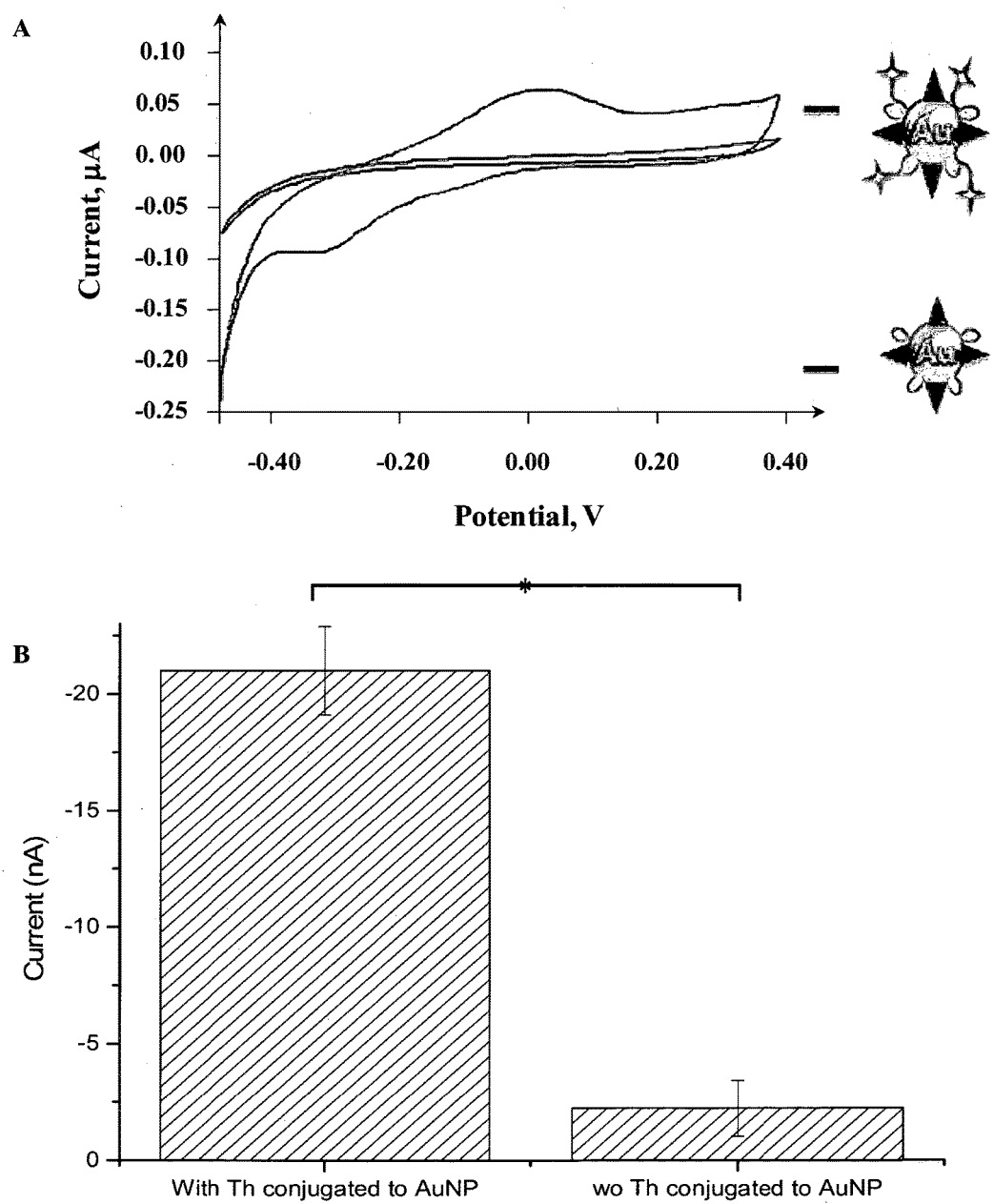
FIG. 13 shows the test for the specificity of the amperometric signal: (A) voltammograms of the gold nanoparticles coated with and without thionine (red and blue line, respectively); and (B) Evaluation of the amperometric signal. T-test for the mean value has a P-Value <0.05. Bars indicate the mean values±standard deviations (n=4).

FIG. 13 shows the recorded and evaluated amperometric signal from the reduction potential of Thionine of each setup: the blue CV represents the setup without Thionine and has no redox peak, while the red CV represents the setup with Thionine and had current peaks at approximately the redox potentials of Thionine. The amperometric signal of the Thionine system is significantly higher compared to the setup without Thionine. The tested analyte was diluted to the lowest tested concentration, and the resulting amperometric signal was still significantly higher compared to the background noise.

Analyte Detection Using ELFB

Figure 14:
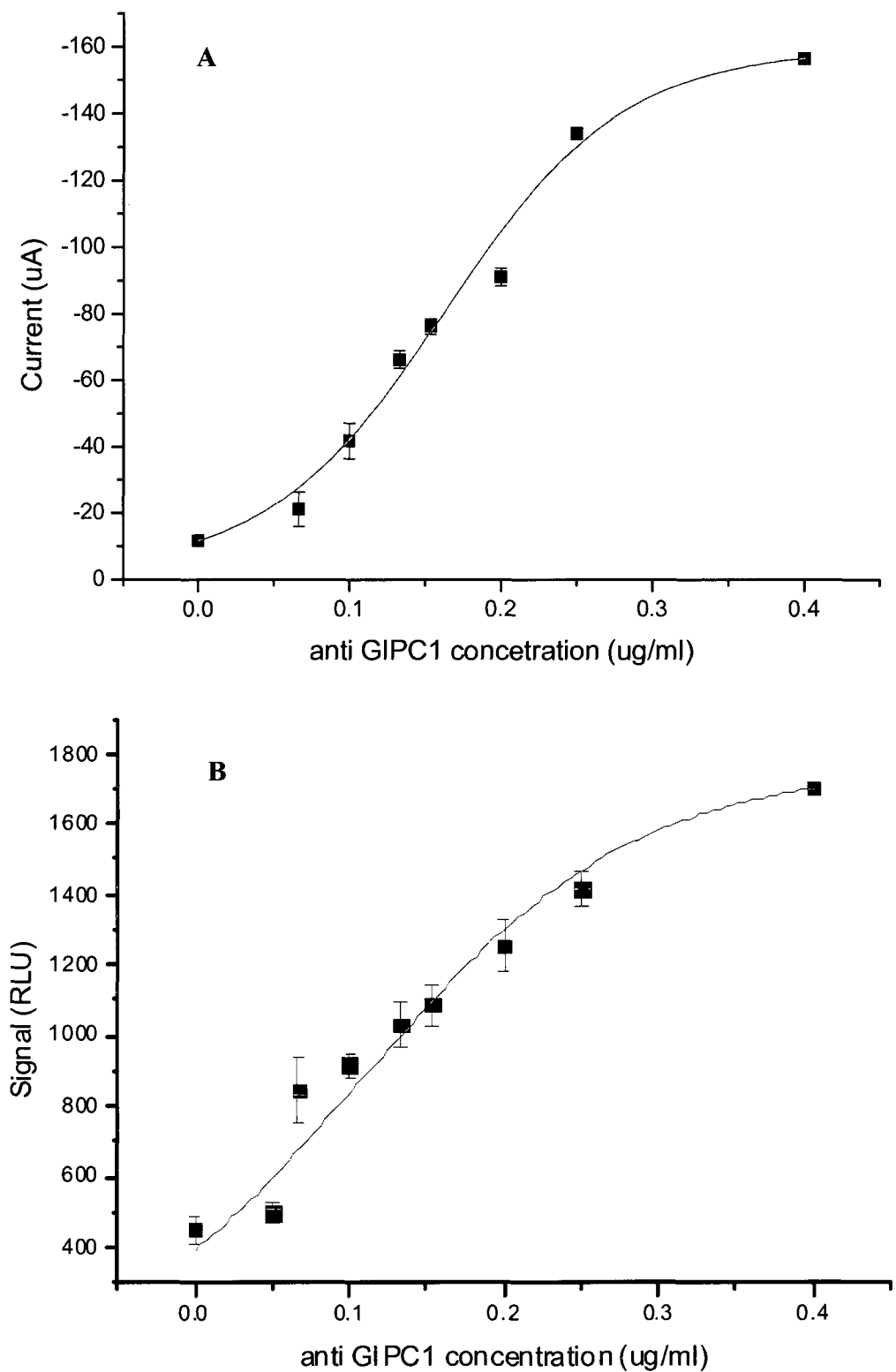
FIG. 14A shows the calibration of the ELFB device to different concentrations of the goat anti-GIPC1 antibody (0.40-0.064 ml, dilutions range from 1:500 to 1:3,000). The amperometric signal was translated into current values (Y axis). The series of results was plotted and fitted to a sigmoid curve ($R^2$=0.99571). Bars indicate the mean values±standard deviations (n=4).
FIG. 14B shows the measurements of the chemiluminescent ELISA response to different concentrations of goat anti-GIPC1 (dilutions range from 1:500 to 1:4,000), for comparison. The optical signal was translated to RLU values (Y axis).

In order to demonstrate the ELFB device capabilities and evaluating the detection ability of the sensor, the commercially available goat anti-GIPC1 antibodies have been measured in the range of concentration 0.40-0.06 µg/ml. In this experiment all the variables were set as constants except for the concentration of the tested analyte. In order to estimate how close the desired sigmoid behaviour can be achieved, the generated current has been plotted as a function of the anti-GIPC1 concentration, as shown in FIG. 14A. The $R^2$ value of indicates the reliability of the sigmoid fitting. The linear section of the curve shows the sensitivity of the biosensor. The lowest concentration of the linear range (or the highest dilution) represents the lowest limit of the biosensor sensitivity.

Overall behaviour of the curve in FIG. 14A is well fitted to the sigmoid plot ($R^2$=0.99571). The analyte concentrations of 0.4 and 0.06 µg/ml were out of the linear area of this sigmoid plot. It means those concentrations are not in the range of the ELFB sensitivity. The linear range shows the lowest and highest sensitivity values of the ELFB system, which are 100 ng/ml (dilution of 1:2000) and 260 ng/ml (dilution of 1:800), respectively. The reasonably small standard deviation values indicate the good reproducibility of the sensor.

The detection ability of the ELFB was compared to the standard chemiluminescent ELISA by testing the same goat anti-GIPC1 antibodies. FIG. 14B relates the optical signal to the changes in the concentration of the target analyte. The linear behaviour of the section of this sigmoidal plot shows the sensitivity area of the chemiluminescent ELISA for the detection of the goat anti-GIPC-1 antibody. The lowest and highest sensitivity values of the ELFB system were obtained from the linear range and were 67 ng/ml (dilution of 1:3000) and 260 ng/ml (dilution of 1:800) respectively. Thus, the obtained sensitivity of the ELFB working prototype is found to be similar to the standard commercial ELISA kit for GIPC1 detection.

ELFB Device Specificity in Comparison to ELISA

Figure 15:
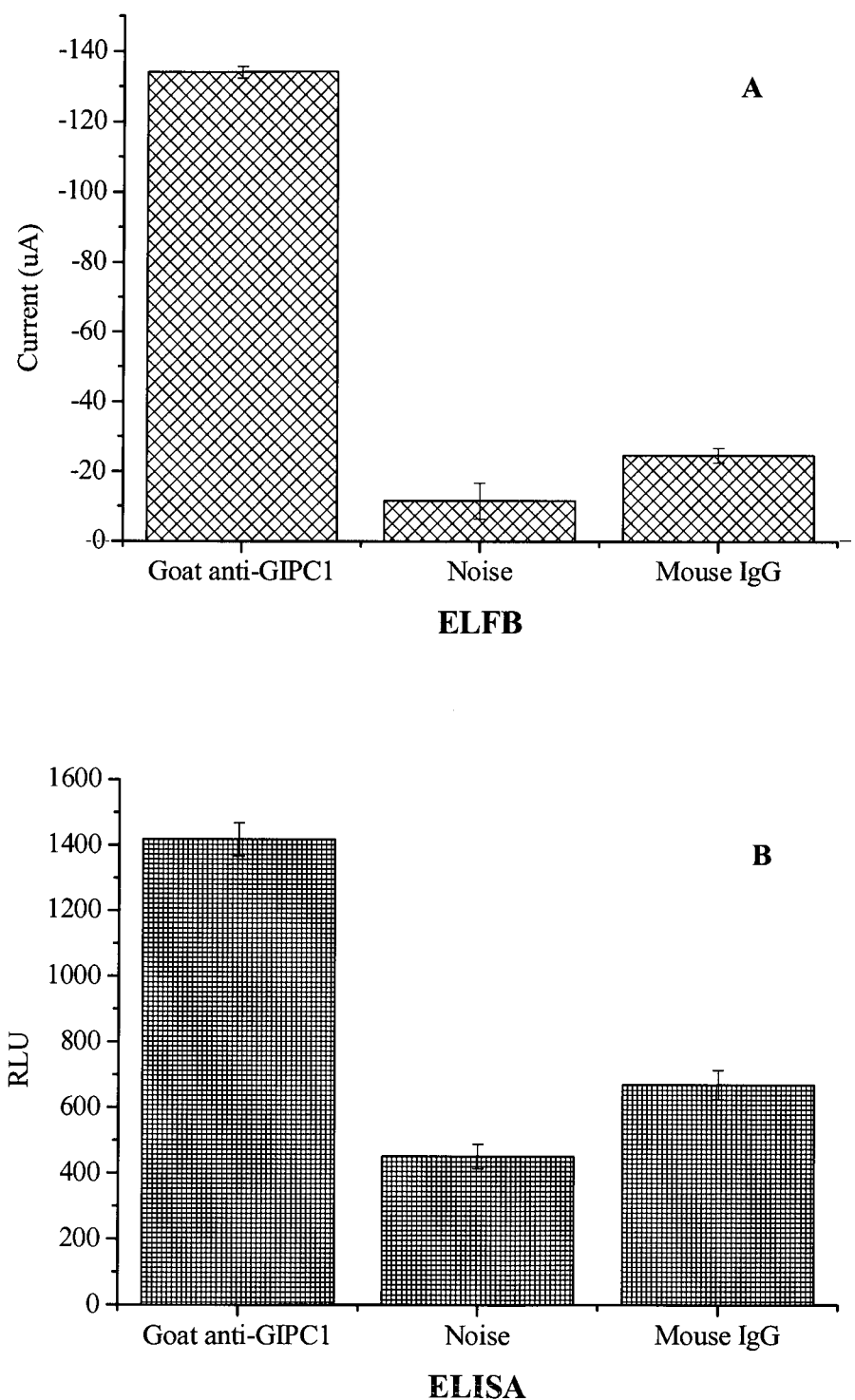
FIG. 15 shows the ELFB specificity test (A) in comparison to the ELISA test (B). T-test for the mean value in both cases has a P-Value <0.05. Bars indicate the mean values±standard deviations (n=4).

In order to test the specificity of the ELFB, mouse IgG antibodies were diluted in PBS (1:500) and examined. The obtained signal was compared to the optimal dilution (1:800) of the ELFB analyte that was obtained from the highest signal of the linear calibration curve and to the background noise using the t-test for the mean value. The specificity of the ELFB was compared to an ELISA test with the same parameters. FIG. 15 presents the obtained amperometric signals of both the ELFB device (A) and ELISA test (B). The target analyte current in the ELFB was 133 µA which was almost six times higher than the recorded current of the non-specific analyte. The background noise was almost 10 times lower than the target analyte signal. As to the ELISA test (B), the obtained optical signal of the target analyte was 1414RLU that is almost 2.5 times higher than the non-specific analyte. In addition, the obtained background noise for the ELFB is significantly lower than that of the ELISA optical test.

Various aspects of the various embodiments disclosed herein are combinable with the other embodiments disclosed herein. Although portions of the discussion herein may relate to chromatography "strips", embodiments of the invention are not limited in this regard, and may include, for example, chromatography units, chromatography elements, chromatography components, chromatography testers, or the like, which may be strip-shaped, non-strip-shaped, or may have various suitable shapes and dimensions.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An electrochemical lateral flow biosensor (ELFB) strip comprising:
    (a) a polymeric hydrophobic membrane, wherein said membrane provides a solid support and enables a capillary flow of a liquid sample along the strip;
    (b) a conjugation pad, wherein said conjugation pad is positioned over and in contact with said membrane at a first end of said membrane and said conjugation pad contains adsorbed dehydrated labelled conjugate particles,
    wherein said conjugate particles are coated with a biorecognition element of an assay and are coated or filled with an electrochemically active component (EAC);
    (c) a sampling pad, wherein said sampling pad is positioned on top of and in contact with said conjugation pad and provides adsorption of the liquid sample;
    (d) a screen-printed electrode (SPE), wherein said SPE is placed in contact with said membrane at a second end of said membrane and said SPE is coated with immobilised capture antibodies, wherein said EAC of said conjugate particles is configured to transfer electrons to said SPE upon binding of said biorecognition element to said immobilised capture antibodies; and
    (e) a wick pad, wherein said wick pad is positioned on top and in contact with said SPE and provides absorption of excess reagents and maintains a lateral flow of the liquid sample along the strip.

2. The strip according to claim 1, wherein said membrane is selected from nitrocellulose, cellulose, or cellulose acetate membrane.

3. The strip according to claim 1, wherein said conjugation pad is made of cross-linked silica, fibreglass, polyester or rayon.

4. The strip according to claim 1, wherein said conjugate particles are colloidal gold particles or coloured, fluorescent, or paramagnetic mono dispersed polymeric particles.

5. The strip according to claim 4, wherein said colloidal gold particles are red-coloured gold nanoparticles or wherein said coloured, fluorescent, or paramagnetic mono dispersed polymeric particles are blue-coloured latex particles.

6. The strip according to claim 1, wherein said biorecognition element is an antigen, an antibody, deoxyribonucleic acid (DNA), an aptamer, a molecular imprint, a lectin, or a ligand.

7. The strip according to claim 1, wherein said EAC is thionine, ferrocene, an electroconductive polymer or polymer combinations, or a combination of suitable redox molecules.

8. The strip according to claim 7, wherein said conjugate particles, coated with ferrocene, are adsorbed onto said conjugation pad coated with hexacyanoferrate ions.

9. The strip according to claim 7, wherein said conjugate particles, coated with ferrocene and hexacyanoferrate ions, are adsorbed onto said conjugation pad.

10. The strip according to claim 1, wherein said SPE is placed over along and in contact with the polymeric hydrophobic membrane at the second end of the membrane, opposite to the conjugation pad.

11. The strip according to claim 1, wherein said SPE is screen-printed directly onto said membrane at the second end of said membrane, opposite to the conjugation pad.

12. The strip according to claim 1, where said SPE comprises one or more working electrodes.

13. An ELFB device comprising:
    (a) a casing or frame inside which is positioned the strip of claim 1; and
    (b) an electronic detector unit, to which said strip is connected using cable or wirelessly.

14. The device according to claim 13, wherein said electronic detector unit is a potentiostat or galvanostat with an electrochemical sensor interface.

15. The device according to claim 13, further comprising a transmitter and an antenna for transmitting data from the device to an external system.

16. A method for assembling the ELFB device of claim 13 comprising:
    (a) preparing the biorecognition element;
    (b) surface functionalizing the conjugate particles and immobilizing said biorecognition element onto a surface of the conjugate particles;
    (c) preparing the conjugate particles by either:
        i. immobilizing the EAC onto the surface of the conjugate particles; or
        ii. introducing the EAC inside the conjugate particles, wherein said conjugate particles are porous polymeric particles capable of releasing said EAC at an electrode through turning on of a voltage;
    (d) coating the surface of the conjugate particles with a first blocking agent in order to prevent non-specific bindings;
    (e) functionalizing a surface of the SPE and immobilizing the capture antibodies onto the surface of the SPE, wherein the EAC of the conjugate particles is configured to transfer electrons to the SPE upon binding of said biorecognition element to said immobilised capture antibodies;
    (f) coating the surface of the SPE with a second blocking agent in order to prevent non-specific bindings;
    (g) placing the membrane on a bottom part of the casing or frame;
    (h) dipping the conjugation pad into a liquid mixture of the conjugate particles prepared in steps (a)-(d), drying the conjugation pad and placing the conjugation pad over and in contact with the membrane, at one end of the membrane;
    (i) placing the sampling pad over and in contact with the conjugation pad;

(j) placing the SPE modified in steps (e)-(f) over and in contact with the membrane, at the second end of the membrane, opposite to the conjugation pad;

(k) placing the wick pad over and in contact with the SPE;

(l) closing the casing or frame with an upper part (cover) and connecting the electronic detector unit to the SPE.

17. The method of claim 16, wherein at least one of said blocking agents is bovine serum albumin (BSA), casein or any suitable detergent.

18. An ELFB diagnostic system comprising the device of claim 13, an external receiver/recorder configured to receive data transmitted by the device, and a computing platform or workstation configured to store, process, display, or analyse the received data.

19. A method for the detection, analysis or diagnostics of bacterial, parasitic, viral infections, tumours and/or other biological bodies in at least one of a wastewater, a physiological liquid or a biological liquid, using the diagnostic system of claim 18, comprising the following steps:

(a) collecting the liquid sample from the at least one of the wastewater, physiological liquid, or biological liquid;

(b) dropping the liquid sample on the strip; and (c) acquiring an amperometric signal with said electronic detector unit.

20. The method according to claim 19, further comprising transmitting the acquired amperometric signal to an external receiver/recorder, and analysing said signal.

21. A method for the detection, analysis or diagnostics of toxins, mycotoxins, explosives and/or other pollutants in at least one of a wastewater, a physiological liquid or a biological liquid using the diagnostic system of claim 18, comprising the following steps:

(a) collecting a sample from at least one of the wastewater physiological liquid or biological liquid;

(b) dropping the sample on the ELFB strip; and (c) acquiring an amperometric signal with an electronic detector unit.

22. The method according to claim 21, further comprising transmitting the acquired amperometric signal to an external receiver/recorder, and analysing said signal.

\* \* \* \* \*